United States Patent [19]
Thomas et al.

[11] Patent Number: 5,849,262
[45] Date of Patent: Dec. 15, 1998

[54] BIOASSAY SYSTEM FOR ARTHROPODS WHICH ELASTICALLY ATTACHES TO AN ANIMAL

[75] Inventors: Rex E. Thomas; Lynda Wallenfels; Irene Popiel, all of Ft. Collins, Colo.

[73] Assignee: Heska Corporation, Fort Collins, Colo.

[21] Appl. No.: 243,286

[22] Filed: May 17, 1994

[51] Int. Cl.$^6$ .......................... A61K 49/00; A01K 29/00; A62B 35/00; A01M 1/20
[52] U.S. Cl. .............................. 424/9.1; 119/6.5; 119/6.6; 119/654; 119/653; 119/863; 119/865; 119/864; 43/107; 43/121
[58] Field of Search .............................. 119/6.5, 6.6, 863, 119/865, 654, 653, 416, 417, 106; 206/524.1, 524.3, 524.6; 424/411, 405, 9.1; 43/107, 121; 514/875, 876

[56] References Cited

U.S. PATENT DOCUMENTS

| | | | |
|---|---|---|---|
| 4,850,305 | 7/1989 | Georgi et al. | 119/1 |
| 4,900,876 | 2/1990 | Bushman et al. | 119/106 |
| 4,967,698 | 11/1990 | Kennedy | 119/106 |
| 5,133,289 | 7/1992 | Georgi | 119/6.6 |
| 5,381,557 | 1/1995 | Luria et al. | 2/16 |

FOREIGN PATENT DOCUMENTS

WO 93/11790  6/1993  WIPO .

OTHER PUBLICATIONS

Dryden, Dissertation, pp. 68–71, in "Blood Consumption and Feeding Behavior of the Cat Flea, *Ctenocephalides felis felis* (Bouché 1835)", Purdue University, May, 1990.
Dryden, pp. 23–27, 1989, *Companion Animal Practice*, vol. 19, No. 3.
Dryden, pp. 117–122, 1989, *Vet. Parasit.*, vol. 34.
Hink et al., pp. 424–427, 1991, *J. Med. Entomol.*, vol. 28, No. 3.
Hudson et al., pp. 1126–1129, 1958, *Bull. Wld. Hlth. Org.*, vol. 19.
Jellison et al., pp. 1081–1082, 1933, *Pub. Health Rep.*, vol. 48, No. 35.
Kern et al., pp. 203–206, 1992, *J. Med. Entomol.*, vol. 29, No. 2.
Osbrink et al., pp. 727–731, 1984, *J. Med. Entomol.*, vol. 21, No. 6.
Silverman et al., pp. 78–83, 1981, *J. Med. Entomol.*, vol. 18, No. 1.

*Primary Examiner*—Gary E. Hollinden
*Assistant Examiner*—Michael G. Hartley

[57] ABSTRACT

The present invention is directed to a bioassay system for retaining hematophagous arthropods, such as, but not limited to, fleas, ticks and flies, in a microenvironment which mimics the natural conditions of unconfined hematophagous arthropods feeding on an animal. The bioassay system of the present invention comprises a container and an attachment means capable of maintaining hematophagous arthropods under conditions such that the fecundity of the retained hematophagous arthropods is substantially equivalent to the fecundity of unconfined hematophagous arthropods. The container is attached to an animal by an attachment means capable of immobilizing the container to the animal in such a manner that hematophagous arthropods can feed undisturbed from the animal through the container. In one embodiment, hematophagous arthropods are retained in a container comprising a retaining means penetrable by the mouth parts of hematophagous arthropods and a gas exchange means. The present invention also relates to the use of the bioassay system to identify agents capable of inhibiting hematophagous arthropod infestation. The bioassay system of the present invention can be part of a kit used to identify anti-hematophagous arthropod infestation agents.

50 Claims, 2 Drawing Sheets

BIOASSAY SYSTEM FOR ARTHROPODS WHICH ELASTICALLY ATTACHES TO AN ANIMAL

FIELD OF THE INVENTION

The present invention relates to a product and method for maintaining hematophagous arthropods in a closed system which mimics the natural conditions of hematophagous arthropods that feed freely on an animal.

BACKGROUND OF THE INVENTION

Hematophagous, or blood-sucking, arthropod infestation of animals is of health and economic concern because hematophagous arthropods are known to cause and/or transmit a variety of diseases. For example, fleas cause and/or carry, for example, flea allergy dermatitis, anemia, murine typhus, plague and tapeworm; ticks are vectors for a broad variety of viruses, rickettsiae, protozoa and spirochetes, leading to, for example Lyme disease, Rocky Mountain spotted fever, Colorado tick fever, relapsing spirochetoses, babesiosis and tularemia; mosquitos are vectors for, for example, heartworm, malaria and several equine and human encephalitis viruses; black flies are vectors for, for example, onchocerciasis; Culicoides sp. biting gnats transmit, for example, bluetongue virus to sheep. The medical and veterinary importance of hematophagous arthropod infestation has prompted the study of the biology of such arthropods. It is often necessary to feed hematophagous arthropods directly on animals to study, for example, disease transmission, host association, effects of environmental parameters, identification and efficacy of systemic inhibitory agents and reproductive biology. It has been difficult to obtain statistically significant data, and particularly to detect statistical significance in small changes, in direct feeding studies of free-roaming hematophagous arthropods on a host animal because significant numbers of hematophagous arthropods and their eggs often are lost during or after the experiment. Studies in which fleas, for example, have been confined in cages have been flawed because the fleas, as exhibited by fecundity and survival data, are not subjected to a normal environment, thereby leading to statistical errors and difficulties in evaluating results. Low fecundity values can make detection of small but significant statistical changes difficult.

Fecundity values, or levels, have been reported for free-roaming fleas colonized on animals that either were or were not allowed to groom. Such studies have typically been conducted in the following manner. A host animal colonized with fleas is maintained in a cage having a tapered and/or grated bottom below which is a collection jar to trap any fleas, flea eggs or flea feces that are dislodged from the animal, due either to flea abandonment of the host, to removal of fleas from the animal during grooming, or due to the death of the flea. The animal can be either allowed to groom (i.e., to clean itself) or fitted with a collar to prevent grooming. At defined time intervals (e.g., daily), dead fleas and flea eggs are collected and counted. Live fleas can only be collected and counted at the end of the experiment. At that time, fecundity values (number of eggs per number of females, typically per unit of time) are determined. According to reports in the literature, fleas roaming freely on unrestrained animals (i.e., animals allowed to groom) exhibited a wide variation in average fecundity values ranging, for example, from 11.3 to 28 eggs per female flea per day (e.g., Osbrink et al., 1984, pp. 727–731, *J. Med. Entomol.*, Vol. 21, No. 6; Smit et al., 1973, pp. 325–371, in Smith, K. G. V., ed., Insects and other arthropods of medical importance, British Museum of Natural History; and Hudson et al., 1958, pp. 1126–1129, *Bull. Wld. Hlth. Org.*, Vol. 19). These values may correspond most closely to natural conditions, except that a significant number of fleas as well as flea eggs can be lost in such an experiment. Loss of fleas and flea eggs has a direct impact on calculating fecundity values.

Dryden et al., 1989, pp. 117–122, *Vet. Parasitol.*, Vol. 34, have reported average fecundity values of 22 to 27 eggs per female flea per day for fleas colonized on restrained animals (i.e., animals not allowed to groom). Maximum flea fecundity values, which refers to fecundity measurements on the day that the fleas laid the most eggs, have been reported to range from 31 to 50 eggs per female on that given day (Dryden, 1989, *Vet. Parasitol., ibid.*; and Dryden, 1989, pp. 23–27, *Companion Animal Practice*, Vol. 19, No. 3, March).

In an attempt to better account for all fleas and flea eggs during a feeding study, other investigators have attempted to confine fleas in chambers attached to animals by various means. The most commonly used attachment device has been a collar. The chambers, however, have been susceptible to movement, particularly when they caused irritation to the animal to which they were attached. Such movement precludes a flea from undisturbed feeding such as occurs in a natural environment. In order to study the biology of fleas, the fleas should be allowed to feed without disturbance, or disruption. Osbrink et al., ibid., analyzing fleas maintained in a microcell, have reported average fecundity values of 13.5 eggs per female per day for fleas maintained in microcells attached to collars that were placed around cats' necks. Egg production reached its maximal level at the fourth day in the microcell (22.3 eggs per female flea on that day) and declined thereafter. Average survival times for females and males in the microcells were 11.2 and 7.2 days, respectively. In a more recent experiment, Hink et al., 1991, pp. 424–427, *J. Med. Entomol.*, Vol. 25, No. 3, analyzing fleas maintained in flea cages attached to collars placed around cats' necks, reported fecundity values of 11.7 eggs per female flea per day during the initial three days of a study, 8.8 eggs per female per day during days 7 through 10 and 7.4 eggs per female per day during days 14 through 17. These fecundity values are significantly less than the values obtained for free-roaming fleas, particularly after the first four days.

As can be seen from the examples provided above, current methods of confining fleas on host animals result in a wide variability in data collected, leading to difficulties in analyzing and interpreting such data, particularly in the evaluation of small changes. Such is also the case for studies involving other hematophagous arthropods. As such, there is still a need for a product and method that allows hematophagous arthropods to be confined for direct feeding experiments on animal hosts in an environment that mimics the natural environment of such hematophagous arthropods. Confinement of hematophagous arthropods enables recovery of all adult hematophagous arthropods, and preferably all eggs laid by hematophagous arthropods, thereby leading to more accurate monitoring of hematophagous arthropod populations. Confinement of hematophagous arthropods in an environment that mimics a natural hematophagous arthropod environment enables more accurate monitoring of biological function which can be particularly important when assessing the effectiveness of various agents that are purported to protect animals from infestation from such hematophagous arthropods.

SUMMARY OF THE INVENTION

The present invention generally relates to a bioassay system capable of maintaining hematophagous arthropods in a closed system which mimics the natural conditions of hematophagous arthropods able to feed freely on an animal (i.e., unconfined hematophagous arthropods). The novel design of the bioassay system of the present invention has resulted in the elucidation of a product and method for maintaining hematophagous arthropods in an environment substantially equivalent to that of unconfined hematophagous arthropods. In particular, the present invention provides for a product and method for evaluating survival as well as fecundity of hematophagous arthropods over time. Suitable hematophagous arthropods to study include, but are not limited to, blood-sucking insects and arachnids, such as fleas, ticks, flies, lice and true bugs, with fleas, ticks and flies being preferred, and with fleas being particularly preferred.

One aspect of the present invention relates to a bioassay system for hematophagous arthropods comprising at least one (i.e., one or more) container capable of retaining such hematophagous arthropods, and preferably also being capable of retaining eggs laid by the hematophagous arthropods, as well as a means for attaching such a container to an animal in such a manner that hematophagous arthropods retained in the container can feed undisturbed on the animal through the container. The fecundity of the retained hematophagous arthropods is at least about substantially equivalent to the fecundity of unconfined hematophagous arthropods. When attached in such a manner, the number of eggs produced per female on about the fourth day of retention in the bioassay system is substantially equivalent to the number of eggs produced per female on about the fourteenth day of retention in the bioassay system. Fleas retained in such a bioassay system, for example, produce an average of at least about 18 eggs per female flea per day from about the fourth day of retention through about the seventh day of retention, and preferably produce an average of at least about 18 eggs per female flea per day from about the fourth day of retention through about the fourteenth day of retention.

The survival rate of hematophagous arthropods retained in bioassay systems of the present invention is at least substantially equivalent to the survival rate of unconfined hematophagous arthropods. Preferably, the survival rate of hematophagous arthropods maintained in bioassay systems of the present invention for at least about 7 days is at least about 90 percent. More preferably, at least about 70 percent of confined hematophagous arthropods survive for at least about 14 days.

Bioassay systems of the present invention are able to mimic natural conditions of unconfined hematophagous arthropods by maintaining a humidity and temperature level such that the fecundity of hematophagous arthropods retained in the system is at least about substantially equivalent to the fecundity of unconfined hematophagous arthropods. Preferred humidities range from about 60 percent relative humidity to about 95 percent relative humidity, whereas preferred temperatures range from about 25° C. to about 30° C.

Containers of bioassay systems of the present invention comprise a material that enables the container to maintain a permissive microenvironment for hematophagous arthropods retained within such containers. A container of the present invention comprises at least one material selected from the group consisting of metallic mesh, nylon mesh, plastic, glass, and wood materials. In one embodiment, a container of the present invention comprises a retaining means penetrable by hematophagous arthropod mouth parts operatively connected to a means for exchanging gas, humidity and heat between the interior environment of the container and the exterior environment. The retaining means and the gas exchange means preferably comprise a nylon mesh material. The retaining means preferably comprises a nylon mesh having from about 0.25 mm to about 0.50 mm openings and the gas exchange means preferably comprises a nylon mesh having from about 0.10 mm to about 0.45 mm openings. Containers of the present invention preferably have a height of from about 1 cm to about 5 cm.

A bioassay system of the present invention further comprises an attachment means capable of allowing the exchange of gas, heat and humidity such that the fecundity of hematophagous arthropods confined within a container of the bioassay system is at least substantially equivalent to the fecundity of unconfined hematophagous arthropods. A preferred attachment means of the present invention comprises a bandage having sufficient size to wrap around the torso of an animal and to hold a container of the present invention against the skin of the animal and a wrapper operatively connected to the bandage which is capable of immobilizing the container against the animal. Preferred bandages comprise at least one material selected from the group consisting of cloth, plastic, tape and harnesses. Elastic bandages are more preferred and tubular surgical stockinettes are even more preferred. Preferred wrappers are self-adhesive, with Vetrap® and Coban® being particularly preferred.

Attachment means of the present invention can also be used to immobilize on an animal a holder capable of maintaining hematophagous arthropods within an area encompassed by the holder by immobilizing the holder on the animal without irritating or injuring the animal, the container and attachment means being reversibly detachable without injuring the animal.

Animals suitable for use in bioassay systems of the present invention include any animal that is susceptible of infestation by a hematophagous arthropod. Such animals include, but are note limited to cats, dogs, rabbits, humans, guinea pigs, sheep, cattle, goats, swine, rats, raccoons and opossums, and more preferably is a cat or a dog. Containers of the present invention are preferably attached to a site on the animal such that the animal is not disturbed, or irritated, by the presence of the container. As such, containers are preferably attached to the lateral side, such as to the rib cage and/or the abdomen of an animal.

Bioassay systems of the present invention have a number of uses including monitoring hematophagous arthropod survival and testing agents for their efficacy in protecting an animal from infestation by one or more hematophagous arthropods.

According to the present invention survival of a hematophagous arthropod can be evaluated by: (a) attaching to an animal at least one container capable of retaining hematophagous arthropods by a means for attaching the container to the animal such that hematophagous arthropods retained in the container can feed undisturbed on the animal through the container; (b) keeping the container attached on the animal for a period of time sufficient to determine the survival rate of the hematophagous arthropods, the container having a known number of hematophagous arthropods retained therein; and (c) assessing the number of live hematophagous arthropods remaining after an appropriate amount of time and comparing the number to the initial number of live hematophagous arthropods in the container. Using such a bioassay system, it is also possible to identify agents such as vaccines, drugs, hematophagous arthropod pathogens, systemic pesticides and hematophagous arthropod hormones capable of inhibiting hematophagous arthropod infestation.

Another aspect of the present invention relates to a kit to determine the ability of an agent to inhibit hematophagous arthropod infestation, such kit comprising a bioassay system of the present invention and a means to determine the ability of the agent to inhibit hematophagous arthropod infestation.

The present invention also includes a method to determine the ability of an agent to protect animals from hematophagous arthropod infestation. The method includes the steps of (a) attaching to animals treated with the agent and to untreated animals one or more containers capable of retaining hematophagous arthropods by a means for attaching the containers to the animals such that hematophagous arthropods retained in the containers can feed undisturbed on the animals through the containers, and (b) determining the ability of the agent to protect the treated animals from hematophagous arthropod infestation by keeping the containers attached on the treated and untreated animals for a sufficient amount of time to determine the survival rate of hematophagous arthropods and by comparing the survival rate of hematophagous arthropods retained in containers attached to the treated animals with the survival rate of hematophagous arthropods retained in containers attached to the untreated animals. The agent can be identified as an inhibitory agent if the survival rate of hematophagous arthropods retained in containers attached to the treated animals is lower than the survival rate of hematophagous arthropods retained in containers attached to the untreated animals. Also included in the present invention are inhibitory agents identified by such a method.

The present invention also includes a method to test an animal's resistance to challenge by a hematophagous arthropod. The method includes (a) attaching to said animal at least one container capable of retaining hematophagous arthropods by a means for attaching the container to the animal such that hematophagous arthropods retained in the container can feed undisturbed on the animal through the container, (b) keeping the container attached on the animal for a sufficient amount of time to determine the survival rate of the hematophagous arthropods, the container having a known number of hematophagous arthropods therein, and (c) assessing the number of live hematophagous arthropods after the amount of time and comparing the number to the initial number of live hematophagous arthropods in the container.

Other aspects and embodiments of the present invention will become obvious to one of ordinary skill in the art after consideration of the drawings and detailed description provided below.

DETAILED DESCRIPTION

Figure 1:
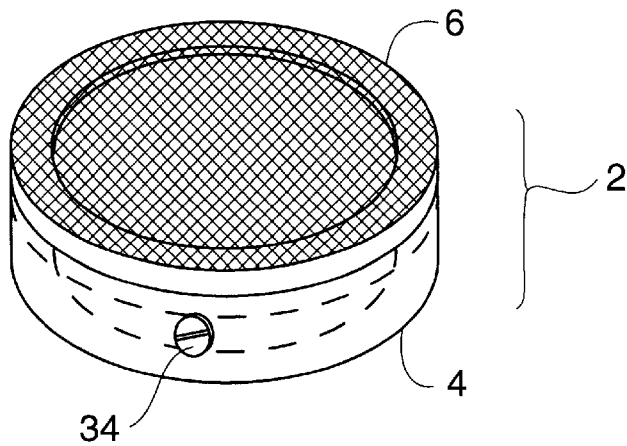
FIG. 1 is a schematic representation of a container of the present invention.

The present invention includes a product and method useful in the development of agents to protect animals from infestation by hematophagous arthropods. The invention is particularly advantageous in that it provides an assay to identify efficacious anti-hematophagous arthropod agents in a simpler manner and at reduced cost compared to current assays. The present invention provides a novel product and method to retain, or confine, hematophagous arthropods, and preferably eggs laid by the hematophagous arthropods as well, during direct feeding experiments in an environment that mimics (i.e., is similar to) the natural environment of the hematophagous arthropods being studied.

One embodiment of the present invention is a bioassay system that includes a container capable of retaining hematophagous arthropods and a means for attaching the container to an animal in such a manner that hematophagous arthropods retained in the container can feed undisturbed on the host animal through the container. As such, a bioassay system of the present invention is capable of retaining hematophagous arthropods in a permissive microenvironment which mimics the natural environment of the hematophagous arthropods. As used herein, the phrase "capable of retaining hematophagous arthropods" refers to the ability of the container to retain essentially all hematophagous arthropods within the container so that an accurate accounting of hematophagous arthropod survival can be obtained during a study. According to the present invention, the phrase "to retain hematophagous arthropods" refers to securing, or holding, hematophagous arthropods within a bioassay system of the present invention. It should be appreciated that the terms retaining, confining and containing can be used interchangeably and that each is intended to refer to securing hematophagous arthropods within a bioassay system of the present invention. Preferably about 100 percent of all hematophagous arthropods are retained in the container. In a preferred embodiment, eggs laid by retained hematophagous arthropods are also retained in containers of the present invention. Preferably about 100 percent of the eggs laid are retained in the containers.

As used herein, the terms "hematophagous arthropod feeding," or "feeding by hematophagous arthropods", each refers to the ability of hematophagous arthropods to feed from or on an animal. The ability of hematophagous arthropods to feed undisturbed refers herein to the ability of hematophagous arthropods to feed without disruption, as would be expected in a natural environment. In order to accomplish undisturbed feeding, a container of the present invention is immobilized on an animal, as will be disclosed in more detail below. The ability of hematophagous arthropods to feed undisturbed can be evaluated in a variety of ways including, but not limited to, determining fecundity, survival rate and/or feces production. Fecundity, for example, can be directly correlated with a hematophagous arthropod's ability to feed. "Normal" fecundity values can indicate "normal" feeding behavior. Thus, fecundity values can indicate either the quantity of blood imbibed, the quality of a blood meal, or the presence of agents inhibitory of blood meal processing.

The present invention includes a novel bioassay system that maintains a permissive microenvironment compatible with the normal lifestyle of hematophagous arthropods. As used herein, the term maintaining refers to sustaining hematophagous arthropods in a permissive microenvironment which influences the survival and fecundity of the hematophagous arthropods during the time the hematophagous arthropods are confined in the bioassay system. As used herein, a permissive microenvironment is an environment in which hematophagous arthropods, although confined, display essentially the normal biological functions of unconfined hematophagous arthropods.

Suitable hematophagous arthropods to study using bioassay systems of the present invention include any blood-sucking arthropod. Preferred hematophagous arthropods to study include, but are not limited to, blood-sucking insects and arachnids. Such preferred hematophagous arthropods include, but are not limited to fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges, mosquitos, sand flies, black flies, horse flies, deer flies, tsetse flies, stable flies, myiasis-causing flies and biting gnats); lice; and true bugs, such as bed bugs and kissing bugs, including those carrying Chagas disease). Fleas, ticks and flies are preferred hematophagous arthropods to study in bioassay systems of the present invention, with fleas being particularly preferred. Although fleas are often used in the examples disclosed herein, it should be noted that bioassay systems of the present invention are eminently suitable for other hematophagous arthropods. For example, soft ticks feed very much like fleas and are difficult to study in known systems (e.g., old-style bottomless tick chambers) because they move very rapidly and are hard to handle. Flies and true bugs also have behavioral characteristics similar to fleas. As disclosed herein, bioassay systems of the present invention can also accommodate hard ticks and lice.

Hematophagous arthropods exhibit certain biological functions that indicate the permissiveness or suitability of the environment in terms of the livability of such an environment. Such biological functions include, but are not limited to, fecundity, survival rate and feeding. Fecundity, as used herein, refers to the number of eggs produced by female hematophagous arthropods during a period of time. Fecundity can be measured using techniques known to those skilled in the art and can be expressed in a variety of ways, including total eggs produced per unit time (e.g., total eggs produced per day) or eggs produced per female per day. Hematophagous arthropods producing larger numbers of eggs per day are characterized as being more fecund than hematophagous arthropods producing lower number of eggs per day. Fecundity can be reported as an average fecundity value, in which case the number of eggs laid per day over a number of days is averaged to obtain an average fecundity per day. Fecundity can also be reported as a maximum fecundity value, which is the maximum number of eggs laid in a day over the length of the study. Fecundity values are preferably calculated using the total number of female hematophagous arthropods introduced into the container at the beginning of the study and, as such, include females that have died during the study as well as those that survived. Thus, fecundity values of the number of eggs laid per female per day as calculated herein are conservative values because the calculations do not correct for hematophagous arthropods that die during the course of the study and, as such, do not lay as many eggs as hematophagous arthropods that are alive throughout the study.

One indication that a bioassay system of the present invention maintains hematophagous arthropods in a permissive microenvironment is that female hematophagous arthropods in such a bioassay system exhibit fecundity values at least substantially equivalent to the fecundity of female hematophagous arthropods free-roaming on an animal. As used herein, hematophagous arthropods referred to as "free-roaming" on an animal or "unconfined" are hematophagous arthropods living in a natural, unrestrained environment on a host animal. Free-roaming, or unconfined hematophagous arthropods can colonize and live freely as ectoparasites on warm-blooded host animals. A host animal, as used herein, refers to an animal that an hematophagous arthropod can infest and feed from or on. Unconfined hematophagous arthropods are able to move about the surface of the host animal while feeding through the dermis of the animal. Unconfined hematophagous arthropods can also leave the animal to feed from another animal. As such, unconfined hematophagous arthropods are not subject to parameters that affect confined hematophagous arthropods such as over-crowding and being disturbed while feeding by, for example, the host animal trying to remove the container retaining the hematophagous arthropods. The maintenance of unconfined hematophagous arthropods, however, can be affected by a variety of parameters. For example, unconfined hematophagous arthropods can be subject to changes in the temperature and/or humidity levels of the environment in which the host animal lives. Unconfined hematophagous arthropods usually live on an animal having hair and/or fur and therefore are subject to host grooming. Bioassay systems of the present invention, in contrast, can provide an environment at least as permissive as the environment of unconfined hematophagous arthropods by protecting hematophagous arthropods from host grooming, feeding disruption and variation in environmental temperature and/or humidity levels.

In accordance with the present invention, hematophagous arthropods having fecundity values "at least substantially equivalent" to that of unconfined hematophagous arthropods are female hematophagous arthropods that have fecundity values about the same as, and/or better than, the average egg production per female hematophagous arthropod per day exhibited by female hematophagous arthropods roaming free on animals. Such animals can either be allowed to groom or be restrained from grooming. The inventors have determined, for example, that the average fecundity of fleas that roam freely on animals capable of grooming themselves averages from about 6 to about 8 eggs per female flea per day; these fecundity values are thought to be on the low side due to adult female flea and egg losses. Reports in the literature of average fecundity values vary from 11.3 to 28 eggs per female flea per day, as disclosed in the background section. Osbrink et al., ibid., who report the 11.3 eggs per female flea per day, also comment that lower fecundity values may be more reflective of natural conditions. Suitable average fecundity values for female fleas retained in a bioassay system of the present invention range from about 18.5 to about 24.5 eggs per female flea per day. Preferred average fecundity values range from about 20.7 to about 24.4 eggs per female flea per day. Even more preferred average fecundity values are at least about 20 eggs per female flea per day. It should be noted that average fecundity values represent an average of daily values taken over a number of days. When a flea is first introduced into a container of the present invention, the flea typically feeds for about 1 to about 2 days before producing significant numbers of eggs. Egg production representative of long-term production typically begins at about day 3. Typically, essentially no eggs are produced on day one, about 50 percent of the normal number of eggs are produced on day two, and a normal number of eggs are produced on day three. As such, average fecundity values are usually obtained after the fleas have been retained in a container of a bioassay system of the present invention for at least about three days.

An advantage of the bioassay system of the present invention is its ability to mimic a permissive microenvironment for a long period of time. Preferably, hematophagous arthropods are maintained in the bioassay system for at least about 7 days and more preferably for at least about 14 days. In accordance with the present invention, fecundity values can be averaged from about day 4 through about day 7 or from about day 4 through about day 14 to obtain average numbers of eggs produced per female per day. Preferably, daily fecundity values remain relatively constant during such periods of time, although maximal values for a particular day can occur. A preferred bioassay system of the present invention is one in which the number of eggs produced per female hematophagous arthropod confined in such a system on about the fourth day of retention in a container is substantially equivalent to the number of eggs produced per female on about the seventh day of retention in the container. Even more preferred is a bioassay system in which the number of eggs produced per female confined in such a system on about the fourth day of retention in a container is substantially equivalent to the number of eggs produced per female on about the fourteenth day of retention in a container.

In accordance with the present invention, a suitable average fecundity value for fleas, for example, is at least about 18 eggs per female flea per day from about the fourth day of retention through about the seventh day of retention. A preferred average fecundity value during that time period is at least about 20 eggs per female flea per day, with a value of at least about 22 eggs per female flea per day being even more preferred, and a value of at least about 24 eggs per female flea per day being even more preferred.

In a preferred embodiment, female fleas retained in a bioassay system of the present invention produce an average of at least about 18 eggs per female flea per day from about the fourth day of retention through about the fourteenth day of retention, more preferably an average of at least about 19 eggs per female flea per day from about the fourth day of retention through about the fourteenth day of retention, and even more preferably an average of at least about 20 to about 21 eggs per female flea per day from about the fourth day of retention through about the fourteenth day of retention. Fleas maintained in bioassay systems of the present invention routinely lay at least about two- to three-times as many eggs as do fleas maintained in chambers described by Osbrink et al. (ibid.) or by Hink et al. (ibid.) and do so for significantly longer periods of time. For example, fecundity values for fleas maintained in a chamber as described by Osbrink, et al. (ibid.) can be a mean value of 13.5 eggs per day over a maximum of 12 days. Fecundity values for fleas maintained in a chamber as described by Hink, et al. (ibid.) can be a mean value of 11 eggs per female per day during days 2 and 3.

Another indication that a bioassay system of the present invention maintains hematophagous arthropods in a permissive microenvironment is that the survival rates of hematophagous arthropods in such a bioassay system are at least substantially equivalent to (i.e., similar to and/or better than) the survival rates of hematophagous arthropods roaming free on an animal. The survival rate of hematophagous arthropods, as used herein, refers to the number of hematophagous arthropods alive after a defined period of time divided by the total number of live hematophagous arthropods at the beginning of the defined period of time. Survival rates of unconfined hematophagous arthropods can be determined from the literature, although it should be noted that the rates vary widely. Preferably at least about 90 percent of the hematophagous arthropods initially introduced into a bioassay system of the present invention survive for at least about 7 days. More preferably, at least about 70 percent of the introduced hematophagous arthropods survive for at least about 14 days. In a preferred embodiment using a bioassay system for fleas, at least about 90 percent, more preferably at least about 95 percent, and even more preferably at least about 97 percent, of the fleas initially introduced into a bioassay system of the present invention survive for at least about 7 days. In a more preferred embodiment, a bioassay system of the present invention can support, for at least about 14 days, at least about 70 percent, more preferably at least about 85 percent, and even more preferably at least about 92 percent, of the fleas initially introduced into the system.

The development and maintenance of hematophagous arthropods can be affected by relative humidity and temperature conditions of the permissive microenvironment. Although the details of such microenvironments can be different for different hematophagous arthropods, as is known to one skilled in the art, microenvironments permissive for hematophagous arthropods are, in general, very similar as will be disclosed in greater detail below. Bioassay systems of the present invention are designed to retain hematophagous arthropods in a microenvironment having suitable relative humidity and ambient temperature levels to mimic or approximate a preferred natural environment for such hematophagous arthropods. As used herein, relative humidity refers to the degree of atmospheric water vapor relative to the maximum degree of atmospheric water vapor that results in precipitation. Thus, relative humidity is expressed in percent humidity, wherein 100 percent humidity represents saturation by atmospheric water vapor. Relative humidity levels can vary in the microenvironment relative to temperature levels (e.g., warmer temperatures typically permit higher humidity levels to exist).

Suitable relative humidity and temperature conditions for use in the present invention are conditions at which the fecundity and survival rates of hematophagous arthropods retained in a bioassay system of the present invention are at least substantially equivalent to the fecundity and survival rate of unconfined hematophagous arthropods. Suitable relative humidity conditions range from about 60 percent to about 95 percent relative humidity, with a range of from about 75 to about 85 percent being preferred for most hematophagous arthropods. It should be noted that ticks generally prefer at least about 95 percent humidity. A particularly preferred humidity level is a relative humidity of from about 75 percent to about 80 percent.

Suitable temperatures range from about 25° C. to about 30° C., with a range of from about 27° C. to about 30° C. being preferred. Particularly preferred is a temperature of about 28° C.

In a preferred embodiment, the relative humidity and temperature conditions of a bioassay system of the present invention are kept at a substantially constant level. Preferred humidity and temperature conditions include the humidity and temperature levels a hematophagous arthropod is exposed to on the skin of the animal host and depend, at least in part, on the species of hematophagous arthropod. For example, temperature and humidity conditions can include about 78 percent relative humidity and a temperature of about 28° C. for *Ctenocephalides felis* on a cat.

As heretofore disclosed, one embodiment of the present invention is a bioassay system that includes a container capable of retaining hematophagous arthropods and a means for attaching the container to an animal in such a manner that hematophagous arthropods retained in the container can feed undisturbed through the container. The structure of the container is such that hematophagous arthropods can feed directly from the animal. Preferred containers of the present invention are also capable of retaining eggs laid by the retained hematophagous arthropods. The attachment means immobilizes the container on an animal such that the hematophagous arthropods can feed undisturbed, as indicated by the retained hematophagous arthropods having a fecundity at least substantially equivalent to the fecundity of unconfined hematophagous arthropods. Together, the container and the attachment means are preferably capable of maintaining the hematophagous arthropods at humidity and temperature conditions such that the fecundity and survival rate of the hematophagous arthropods is at least substantially equivalent to the fecundity and survival rate of hematophagous arthropods roaming free on an animal. In addition, the positioning of the container on an animal using the attachment means can be important in achieving "undisturbed conditions", as disclosed in more detail below.

A bioassay system of the present invention provides numerous advantages in hematophagous arthropod challenge studies. For example, accurate numbers of dead and live hematophagous arthropods in a study can be determined because all dead and live hematophagous arthropods can be recovered from the bioassay system. Conversely, the number of dead hematophagous arthropods in a free-roaming system is difficult to determine because a hematophagous arthropod can die, fall off, or be eaten by the animal. Furthermore, a live hematophagous arthropod can leave the animal and could not be accounted for as dead or alive. Challenge studies performed using a bioassay system of the present invention requires less labor than studies using free-roaming hematophagous arthropods on an animal. To determine the fecundity and survival rates of free-roaming fleas, for example, an animal must be combed for at least about 45 minutes to recover the fleas and flea eggs. Such a combing step is not required when using a bioassay system of the present invention. In addition, recovering free-roaming hematophagous arthropods from white animals is easier than from black animals because the hematophagous arthropods are more easily identified on a white animal during combing. Such a distinction is not applicable when using a bioassay system of the present invention.

Containers of bioassay systems of the present invention can be removed and replaced on the same animal at desired time intervals without injuring the animal in order to determine fecundity and survival values over time. Typically, unconfined hematophagous arthropods cannot be replaced on the same animal due to the means of collection. In addition, bioassay systems of the present invention enable hematophagous arthropods to be subjected to different animals during the course of a study.

Moreover, hematophagous arthropod challenge studies can be performed with fewer animals and fewer hematophagous arthropods when hematophagous arthropods are retained in a bioassay system of the present invention rather than free-roaming. Fewer hematophagous arthropods can be used because efficient recovery of hematophagous arthropods and their eggs from bioassay systems of the present invention provides less statistical variation than found in statistics obtained from studies using free-roaming hematophagous arthropods. Thus, fewer animals and fewer hematophagous arthropods can be used in challenge studies using a bioassay system of the present invention.

Because a bioassay system of the present invention is preferably capable of retaining eggs laid by retained hematophagous arthropods, an accurate count of all eggs produced during an appropriate amount of time can be made. Recovery of eggs produced by free-roaming hematophagous arthropods is not as accurate because the eggs can fall off the animal spontaneously or due to animal grooming.

A container of the present invention is capable of retaining hematophagous arthropods and preferably eggs laid by the retained hematophagous arthropods as well. Hematophagous arthropods are capable of feeding directly on a host animal from such a container (i.e., at least a portion of the container is of a material that is penetrable by hematophagous arthropod mouth parts) when the container is attached to the animal by the attaching means. A container of the present invention is also capable of exchanging gas, heat and humidity between the interior environment of the container and the exterior environment (i.e., at least a portion of the container is of a material that enables such exchange). At least a portion of a container of the present invention is also of a structural material that provides dimensions (e.g., height, surface area, volume) to the container to enable a permissive microenvironment for hematophagous arthropods retained therein. In one embodiment, the container is made of one material. In another embodiment, the container comprises more than one material, each of which can be suited for one or more specific functions.

One embodiment of the present invention is a container that includes a retaining means operatively connected to an exchange means. As used herein, "operatively connected" refers to combining a retaining means and an exchange means in such a manner that there is sufficient volume to allow movement of hematophagous arthropods within the container, as well as, in a manner such that hematophagous arthropods, and preferably hematophagous arthropod eggs as well, are retained in the container, but heat, humidity and gases can be exchanged between the interior of the container and the external environment in order to maintain a permissive microenvironment within the container for the hematophagous arthropods retained therein.

In one embodiment, the container can comprise a housing operatively connected to a retaining means and an exchange means. The primary function of the housing is to provide volume and structural support to the container. The housing can comprise any material capable of retaining hematophagous arthropods, and preferably hematophagous arthropod eggs as well, that provides structural support and that can be connected to a retaining means and an exchange means. The housing is preferably made of a material capable of withstanding cleaning or sterilization procedures commonly used by those skilled in the art. As such, the housing can be reused. Preferred housing materials of the present invention include, but are not limited to, plastic, metal, rubber, wood and glass materials and combinations of such materials. More preferred housing materials include plastic and metal materials with plastic materials being even more preferred. Preferred plastic materials include plexiglass, teflon, nylon and polycarbonate. A particularly preferred plastic material is plexiglass, or other durable, break-resistant plastic, preferably clear or white so as to allow viewing of hematophagous arthropods inside the container.

Retaining means of the present invention can comprise any material or combination of materials that is suitable for retaining hematophagous arthropods, and preferably hematophagous arthropod eggs as well, and through which hematophagous arthropods can feed (i.e., the retaining means is penetrable by hematophagous arthropod mouth parts) when the retaining means is placed in contact with the animal host. In one embodiment, the material used as a retaining means can also be used as an exchange means Retaining means can also be used that retain feces.

As such, for hematophagous arthropods that feed without cementing their mouthparts into the host animal, the retaining means preferably comprises a material having openings sufficiently large (i.e., large enough) for hematophagous arthropod mouth parts to penetrate, but sufficiently small (i.e., small enough) so as to effectively prevent loss of hematophagous arthropods or their eggs. Preferred retaining means comprise a material having openings of from about 0.25 millimeters (mm) to about 0.50 mm, more preferably having openings of from about 0.30 mm to about 0.50 mm, and even more preferably having openings of from about 0.35 mm to about 0.45 mm. It should also be noted that maintenance of particularly small hematophagous arthropods such as, but not limited to, lice may require retaining means having smaller openings.

In order to enable undisturbed feeding, retaining means for hard ticks, which are hematophagous arthropods that do cement their mouthparts into the host animal, should have larger openings, preferably about in the range of about 1 mm. Although such openings are likely to be too large to collect eggs, the natural biology of the tick is such that ticks are usually transferred to tubes after engorging blood in order to lay eggs and feces (i.e., ticks typically lay eggs about 1 week after they complete feeding). The engorgement weight of fed ticks, compared to unfed controls, can also be used to assess successful feeding.

Preferred materials for use as retaining means include, but are not limited to, metallic mesh, nylon mesh, plastic, cloth and combinations of such materials. More preferred retaining means include nylon mesh and metal mesh, and an even more preferred retaining means includes nylon mesh. The container can be retrofitted with a variety of retaining means. Preferred retaining means are reusable.

Exchange means of the present invention can comprise any material or combination of materials capable of maintaining, in conjunction with the attachment means, a permissive environment for hematophagous arthropods within the container by allowing the exchange of gas, humidity and heat between the interior environment of the container and the environment exterior to the container. The container can be retrofitted with different exchange means having different gas, humidity and heat permeabilities. As used herein, the term gas refers to any atmospheric gases required for hematophagous arthropod survival, including, but not limited to, carbon dioxide, oxygen, and nitrogen. Gas can also refer to gaseous products produced by hematophagous arthropods while maintained in a bioassay system of the present invention, such as gaseous products of metabolism including expirations or gases from feces.

Exchange means of the present invention are comprised of materials having openings that are sufficiently large to allow gas, heat and humidity to escape, but sufficiently small so as to effectively prevent loss of hematophagous arthropods and, preferably, of eggs laid by retained hematophagous arthropods as well. Preferred exchange means comprise a material having openings of from about 0.10 millimeters (mm) to about 0.45 mm, more preferably having openings of from about 0.10 mm to about 0.30 mm, and even more preferably having openings of from about 0.13 mm to about 0.15 mm.

Preferred materials to use as an exchange means include, but are not limited to, metallic mesh, nylon mesh, plastic, cloth and combinations of such materials. More preferred exchange means include nylon mesh, metal mesh, and combinations of such materials and an even more preferred exchange means includes nylon mesh. Preferred exchange materials are reusable.

In accordance with the present invention, the size of a container of the present invention is such that the container can support a desired number of hematophagous arthropods without overcrowding. Both surface area and the volume of the container can be important. The size of the container can vary according to the number of hematophagous arthropods to be retained in the container and/or to the size of the animal to which the container is to be attached. A number of embodiments can be used depending on the nature of the study for which a bioassay system is being utilized. In a preferred embodiment for a flea bioassay system, the size of the container is sufficient to maintain at least about 50 fleas per container for at least about 7 days. If eggs are being weighed instead of counted, a container sufficient to maintain at least about 100 fleas per container may be preferable since a larger number of fleas can be analyzed per experiment. If a slow-working agent is being tested, a container of a size sufficient to maintain at least about 50, or at least about 100, fleas per container for at least about 14 days is preferred.

A suitable height for a container of the present invention is a height that is sufficiently high to allow room for hematophagous arthropods to move about the container while feeding. A suitable container of the present invention has a height that is tall enough to allow hematophagous arthropods prone to jumping to jump within the container but short enough to minimize movement of the container when attached to an animal. For example, the height of the container is sufficiently low to prevent the animal's natural movement from dislodging the container. The height of the container is preferably from about 1 centimeter (cm) to about 5 cm. For fleas, the height of the container if preferably from about 1 cm to about 3 cm, more preferably from about 1.5 cm to about 2.5 cm, and even more preferably from about 1.8 cm to about 2.2 cm.

The diameter of a container of the present invention can vary widely. Different diameter containers can be used according to, for example, the number of hematophagous arthropods to be placed into the container without overcrowding and the size of the animal. A novel aspect of the present invention is the stability exhibited by containers of the present invention while attached to an animal (i.e., ability of the container to remain essentially immobile when attached to the animal). As such, the diameter or dimensions of a container of the present invention is sufficiently proportionate to the size of the animal such that the container remains immobile while attached to the animal. The interior diameter of a rounded container of the present invention is preferably from about 4.0 cm to about 5.5 cm, more preferably from about 4.5 cm to about 5.5 cm, and even more preferably about 5.0 cm, preferably for use on an animal at least the size of a cat.

In another embodiment, the shape of the container can be any shape having at least one flat surface suitable for being placed against an animal such that hematophagous arthropods contained within the container can feed directly from an animal. A container of the present invention is preferably shaped as a cylinder, a box having four or more sides, a half-dome, or a half cylinder. A particularly preferred shape is a short cylinder.

In yet another embodiment, the weight of a container of the present invention can be any weight sufficiently light to enable the container to be secured by an attachment means to desired portions of an animal in such a manner that prevents unwanted movement of the container while it is attached to the animal. A container can be as light as from about 1 to about 2 grams. Preferred container weights range from about 15 grams to about 40 grams, more preferably from about 20 grams to about 35 grams, and even more preferably from about 25 grams to about 30 grams.

Figure 2:
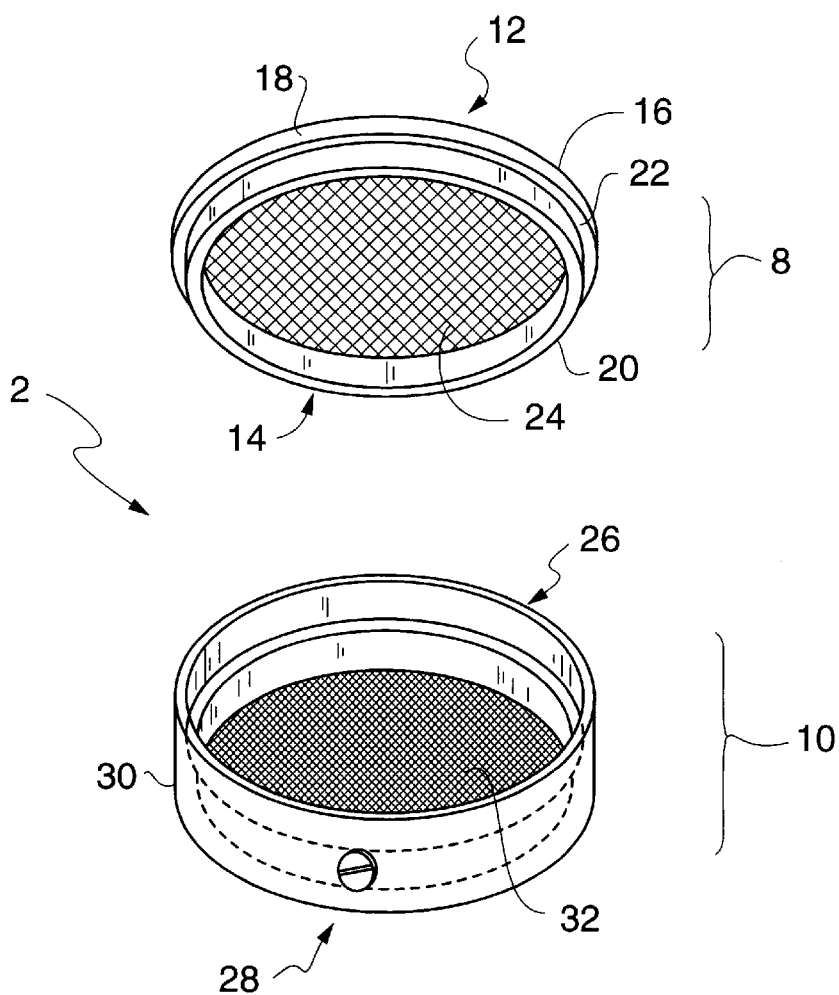
FIG. 2 is a schematic representation of a container of the present invention.

In a preferred embodiment depicted in FIG. 1, a container (2) is constructed using an open-ended cylinder having an exchange means (4) at one end and a retaining means (6) at the opposite end. Referring to FIG. 2, the container, herein referred to as (7), is separable into a first portion (8) and a second portion (10). Although this container is described herein for retaining fleas it is to be understood that such a container can also retain other hematophagous arthropods. The first portion (8) of the container (7) includes a first top end (12), a first bottom end (14), and a first outer wall (16) with a first larger diameter part (18) and a smaller diameter part (20) joined by a downwardly facing shoulder (22). The smaller diameter part (20) defines the diameter of the surface through which fleas can feed. The first top end (12) is covered by the retaining means (24) (indicated as (6) in FIG. 1) and the first bottom end (14) is open.

The retaining means (24) is operatively connected to the first top end (12) in a manner that prevents fleas and/or flea eggs from escaping. The retaining means (24) can be connected to the first top end (12) in order to provide either a permanent or detachable connection. Means of attaching an retaining means (24) to a first top end (12) include, but are not limited to, rubber cement, glue, tape, solder and araldite. A preferred means to attach the retaining means (24) to the first top end (12) is a glue that is capable of fusing plastic and of drying hard such that animal hair or flea material (e.g., eggs, feces and proteins) do not stick to the glue. A more preferred means to attach the retaining means (24) is Duco® airplane glue.

The second portion (10) of the container (7) of FIG. 2 includes a second top end (26), a second bottom end (28), and a second outer wall (30). The second top end (26) is open and the second bottom end (28) is covered by the exchange means (32) (indicated as (4) in FIG. 1). The exchange means (32) is operatively connected to the second bottom end (28) in such a manner that a seal is formed preventing loss of fleas and/or flea eggs. The exchange means (32) can be connected to the second bottom end (28) in order to provide either a permanent or detachable connection. The exchange means (32) can be attached to the second bottom end (28) by a variety of means including, but not limited to, glue, solder, tape, araldite and rubber cement. A preferred means to attach the exchange means (32) to the second bottom end (28) is a glue capable of fusing plastic and of drying hard such that animal hair or flea material (e.g., eggs, feces and proteins) do not stick to the glue. A more preferred means to attach the exchange means (32) is Duco® airplane glue.

The first portion (8) is reversibly separable from the second portion (10). The first portion (8) can be interconnected to the second portion (10) in any reversibly secure manner such as sliding, snapping or screwing together. Preferably, the periphery of the second outer wall (30) of the second portion (10) is selected to abut the smaller diameter part (20) of the first portion (8) in such a manner as to provide a sliding fit with sufficient resistance to require torque applied by both hands to separate the first portion (8) of the container (7) from the second portion (10).

The relative height dimensions of the first portion (8) can vary relative to the second portion (10). Typically, the height dimension of the first portion (8) is less than the second portion (10). Preferably, the height of the first portion (8) ranges from about 0.5 cm to about 2.0 cm, more preferably from about 0.75 cm to about 1.5 cm, and even more preferably from about 0.8 cm to about 1.2 cm. The height of the second portion (10) preferably ranges from about 0.75 cm to about 2.5 cm, more preferably from about 1.0 cm to about 2.0 cm, and even more preferably from about 1.4 cm to about 1.8 cm.

Bioassay systems of the present invention, unlike chambers and other cages reported in the literature, allow hematophagous arthropods to feed undisturbed from or on an animal. As used herein, the term undisturbed refers to the ability of a hematophagous arthropod to feed continuously without any substantial interruption caused by movement of the container since, in accordance with the present invention, the container is attached to the animal in such a way that there is no substantial movement of the retaining means away from the point of dermal penetration by a hematophagous arthropod's mouth parts into the animal. Feeding hematophagous arthropods are sensitive to movement because, in order to feed, a hematophagous arthropod penetrates the dermis of the animal with its mouth parts, the mouth parts remaining in that position while the hematophagous arthropod secretes saliva to prepare the dermal tissue for blood feeding. Fleas, for example, typically feed in the same location for an average of from about 2 to about 20 minutes and can feed at a single location for as long as about 60 minutes (Dryden Dissertation, "Blood Consumption and Feeding Behavior of the Cat Flea, *Ctenocephalides felis felis* (Bouche'1835)", Purdue University, May, 1990)

Unconfined hematophagous arthropods feeding from an animal can be disturbed by the grooming activity of animals such as licking or scratching. Because confined hematophagous arthropods feed through a container surface in order to feed from an animal, feeding by confined hematophagous arthropods can be disturbed by grooming activity as well as by other movements of the animal which often result in significant movement of a container. By evaluating a number of potential means to attach a container to an animal, the inventors have developed a bioassay system, one novel aspect of which is the ability to attach containers to an animal in such a manner that the containers remain immobile, thereby allowing hematophagous arthropods confined in the container to feed undisturbed from an animal. Using such an attachment means, containers of the present invention remain immobile on the animal such that the fecundity and survival rate of hematophagous arthropods maintained in a bioassay system of the present invention is at least substantially equivalent to the fecundity and survival rate of hematophagous arthropods roaming free on an animal. The attachment means of the present invention is such that use of such an attachment means results in containers of the present invention being immobilized in a manner such that the animal is not irritated or injured by the bioassay system. As used herein, the terms to irritate, or irritating, refers to tending to cause physical discomfort such that an animal would attempt to remove the source of discomfort, such as by scratching or biting. Irritation can also cause a change in the animal's behavior, such as increased abnormal movement by the animal, and stress. As used herein, the term injured refers to physical damage to the animal. Such physical damage can include, but is not limited to, sores, roughness, inflammation, cuts, or bruises. According to the present invention, a container can be attached in such a manner that the container does not continually move or does not suddenly move. Preferably, the container of the present invention is attached to an animal in such a manner that the container moves less than about 3.0 cm each day that the container is attached to the animal; more preferably, the container moves less than about 1.5 cm each day; and even more preferably, the container does not move at all. That the container is attached in such a manner as to be immobile can also be determined by monitoring fecundity and survival of hematophagous arthropods retained in the container in order to determine whether such hematophagous arthropods are feeding as they would if they were roaming free on an animal.

One embodiment of a bioassay system of the present invention comprises a means for attachment. As used herein, an attachment means is a means that secures, or fastens, a container of the present invention to an animal. Attachment means of the present invention limit undesired movement of a container while the container is attached to an animal. Stabilization of the container by the attachment means allows hematophagous arthropods retained in such a container to feed relatively undisturbed from an animal. As such, the attachment means secures a container in such a manner that the container remains stationary, or immobile, when the animal moves, and essentially is not knocked off by the animal.

Attachment means of the present invention are adjustable and therefore can be used with a variety of animals. The adjustable nature of the attachment means is important because the attachment means can immobilize a container on an animal without irritating or injuring the animal by, for example, constricting the animal's blood supply or causing cuts and abrasions. The container and attachment means can also be detached from the animal without injuring the animal (i.e., the container is held onto the animal without being physically attached, e.g., glued or taped, onto the animal). Because the container and attachment means are removable and preferably adjustable, containers and attachment means can be reused on animals of similar or different sizes.

In accordance with the present invention, an attachment means combined with an exchange means of the present invention are made of materials capable of maintaining a permissive microenvironment within an attached container by maintaining suitable humidity and temperature conditions permissive for maintenance of a hematophagous arthropod. The attachment means can maintain a permissive environment within a container of the present invention despite changes in the external environment. As such, a suitable attachment means of the present invention comprises one or more materials that allow passage of gas, heat and humidity in and out of a container while immobilizing the container to an animal such that hematophagous arthropods retained in such a container exhibit a fecundity at least substantially equivalent to the fecundity of hematophagous arthropods roaming free on an animal.

A preferred embodiment of the present invention is a bioassay system having a container and an attachment means such that the attachment means includes: (a) a bandage having sufficient size to wrap around the torso or appendage of an animal and that is used to secure the container against the outer skin of the animal and provide protection from a wrapper of the present invention; and (b) a wrapper that is operatively connected to the bandage in order to immobilize the container on the animal. The bandage preferably comprises a closed length of elastic tubing material, but can be of any material that, with the wrapper, immobilizes a container of the present invention on an animal and that allows a permissive microenvironment in that container. Suitable materials to use as a bandage include cloth, plastic, tape, harnesses and combinations thereof. Preferred materials include elastic bandages. A particularly preferred bandage is a surgical stockinette. The relative length of the bandage can vary according to the size of the portion of an animal to which a container is to be attached. For example, the bandage can have sufficient length to be pulled onto an animal so that the bandage covers the torso of the animal. Preferably, the length of the bandage is sufficient to secure the container to the animal while not being too tight to irritate or injure the animal. The relative width of the bandage can vary according to the diameter of the container to be attached to an animal, the attachment site of the container on the animal and the size of the animal. The width of the bandage is at least sufficient to attach a container of the present invention to an animal. Preferably, the width of the bandage is about twice the diameter of the container.

Figure 3:
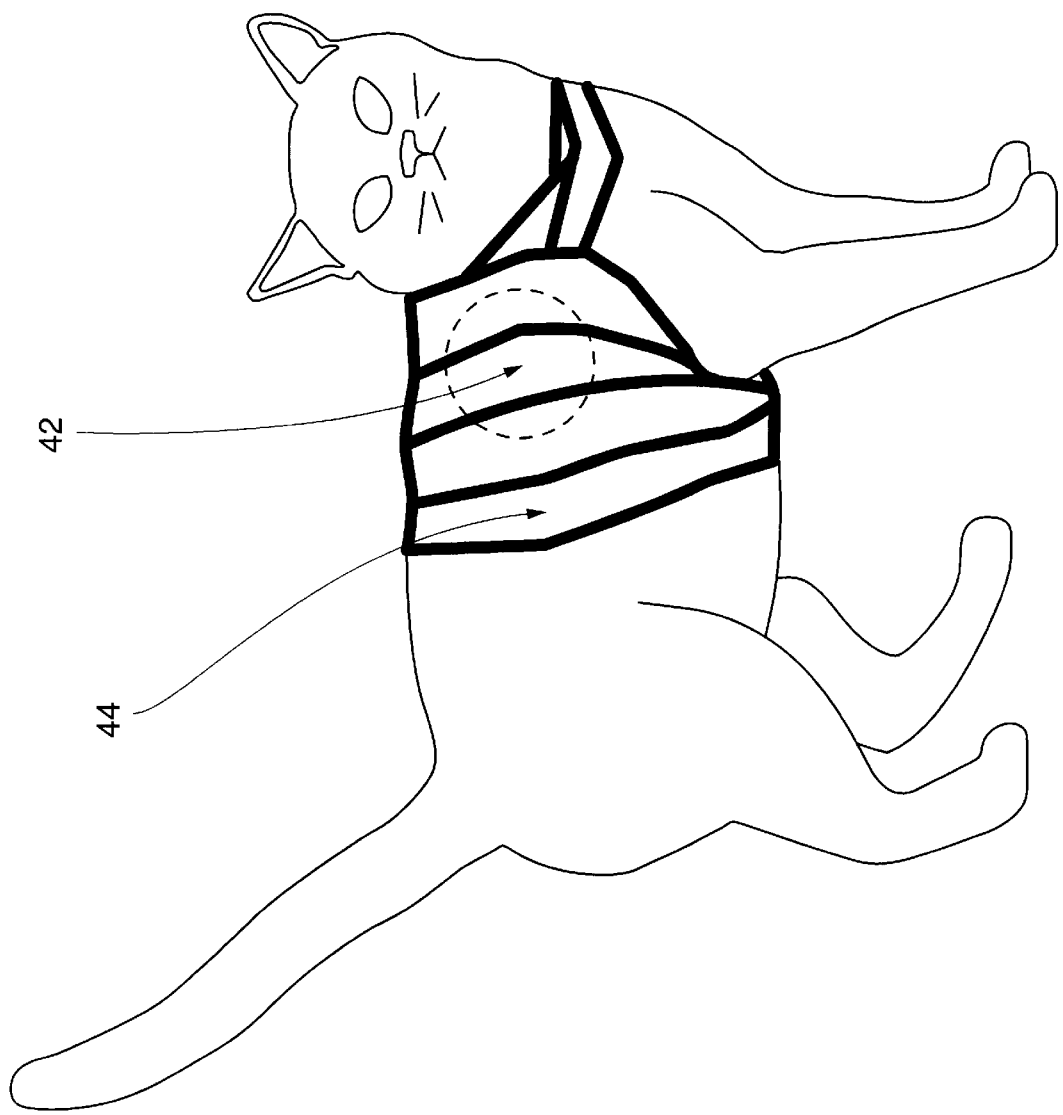
FIG. 3 is a schematic representation of an attachment means of the present invention.

As used herein, the phrase "a wrapper is operatively connected to the bandage" refers to the wrapper being attached to the bandage such that a container of the present invention positioned between the bandage and the outer skin of the animal is immobilized. Preferably a self-adhesive wrapper is used. Suitable wrapping materials are materials that in conjunction with the bandage are capable of immobilizing the container to the animal and that are capable of allowing a permissive microenvironment within the container. Thus, the wrapper and bandage can assist an exchange means by allowing maintenance of temperature and humidity levels within the container. Preferred materials to use as wrappers include Vetrap®, Coban® and combinations thereof. A particularly preferred material to use as a wrapper is Vetrap®, The relative length and width of the wrapper can vary with the size of the animal to which the bandage is attached as well as with the position on the animal that the container is to contact in order to immobilized the container and bandage. For example, a wrapper can be wrapped about 1 to about 2 times around a small animal, and about 3 to about 4 times around a large animal. Typically, the length of the wrapper is sufficient to wrap around the bandage such that a container of the present invention cannot, for example, slide from the rib cage of an animal to the abdomen section. When a container is attached to the rib cage, a wrapper is preferably wrapped around the chest in a cross-wise fashion of an animal first and then around the area to which the bandage is attached. Preferably, the wrapper does not directly contact, or touch, any shaved area (bare skin) of the animal. An example of a preferred bioassay system of the present invention is schematically represented in FIG. 3.

It should also be appreciated that an attachment means of the present invention can also be used to immobilize holders for hematophagous arthropods other than just containers of the present invention without irritating or injuring the animal. In accordance with the present invention such a bioassay system is reversibly detachable (i.e., it can be removed and reattached to one or more animals as many times as desired) without injuring the animal. An example of a holder of the present invention is a device that comprises a housing and an exchange means but that has one side that is open, that side being in contact with the outer skin of the animal, such that hematophagous arthropods are maintained within the area encompassed by the holder when the holder is attached to an animal using an attachment means of the present invention. Such a holder is particularly useful in the study of hematophagous arthropods that cement their mouthparts into the animal (i.e., hard ticks) but conceivably is useful in the study of any hematophagous arthropod. Such a bioassay system is advantageous compared to those known in the art in which a bottomless cage is often taped or glued onto an animal or, if the animal is small enough, the animal is put into a bag with the ticks. Such cages and/or the method of attachment of such cages to the animals can irritate and/or injure animals; moreover, cages that are taped or glued onto an animal are not detachable without injuring the animal and are less convenient for time course studies than are bioassay systems of the present invention.

One embodiment of the present invention is a method to approximate and/or mimic the natural conditions of hematophagous arthropods roaming free on an animal. Such a method can be used, for example, to evaluate hematophagous arthropod survival and feeding behavior. Such a method can also be used to screen for agents that are able to protect an animal from hematophagous arthropod infestation and/or to determine whether an animal is resistant to challenge by hematophagous arthropods. Because the present method both mimics natural conditions for hematophagous arthropods and can account for essentially all hematophagous arthropods and their eggs, even small but consistent differences in efficacy of different inhibitory agents can be considered to be significant because non-specific variations (i.e., losses of hematophagous arthropods and/or eggs) are minimized. The present method includes the steps of (a) attaching to an animal at least one container, or other holder, of the present invention by a means for attaching the container to the animal such that hematophagous arthropods retained in the container can feed undisturbed on the animal through the container and (b) keeping the container attached on the animal for a defined period of time. That hematophagous arthropods are feeding undisturbed can be demonstrated by showing that the attached container is immobile and/or by showing that hematophagous arthropods retained in the container have an average fecundity that is at least substantially equivalent to the fecundity of unconfined hematophagous arthropods.

Any animal susceptible to hematophagous arthropod infestation can be subjected to this method, including, but not limited to, a wide variety of vertebrates. Preferred animals include mammals. More preferred animals include cats, dogs, humans, rabbits, sheep, cattle, swine, goats, raccoons, rats and opossums as well as other pets, economic food animals and animals that are hosts for hematophagous arthropods that infest pets and economic food animals. Particularly preferred animals are cats and dogs.

In one embodiment, a pre-determined number of fleas, or other hematophagous arthropods, are introduced into the container prior to attachment of the container to an animal. Any suitable hematophagous arthropod species can be used. A particularly preferred hematophagous arthropod to study is the flea, although other preferred hematophagous arthropods are also herein disclosed. Preferred fleas to study include fleas capable of infesting cats, dogs, humans, sheep, cattle and goats. Particularly preferred species of fleas for use with the present invention include *Ctenocephalides felis, Ctenocephalides canis, Echidnophaga gallinacea, Pulex irritans, Pulex simulans, Xenopsylla cheopis,* and *Oropsylla* (Diamanus) *montana*. The number of fleas, or other hematophagous arthropods, to be introduced into a container can vary with the size of the container and should be a number that will not lead to overcrowding. Suitable and preferred numbers of fleas, or other hematophagous arthropods, to introduce into a container are heretofore disclosed.

The ratio of male hematophagous arthropods and female hematophagous arthropods added to a container can be any ratio ranging from all females to all males depending on the type of study to be conducted. If fecundity is to be measured, at least some males need to be added in addition to females. It has been found in fleas, for example, that addition of as few as about 5 percent males is sufficient to effect efficient egg laying by the females. Even a smaller male/female ratio is possible as are larger male/female ratios. In some studies in which feeding biology is being studied, it may be preferable to study only female or only male fleas, particularly if one desires to monitor feces production.

In a preferred embodiment of the present invention, a container (2) of the present invention as represented in FIG. 1, is disassembled by removing the first portion (8) from the second portion (10) as shown in FIG. 2. Fleas are placed onto the exchange means (32) of the second portion (10) of the container. Fleas can be anesthetized with $CO_2$ or Metofane® (methoxyflurane) prior to loading. In another embodiment, non-anesthetized fleas can be vacuum loaded into a container in which, referring to FIG. 2, the first portion (8) is already attached to the second portion (10). Referring to FIG. 1, a screw (34) contained in the side of the container (2) can be removed and the container (2) can be placed under a vacuum source such that vacuum can be drawn through the opening provided by the removal of the screw (34) and out the retaining means (6). A tubing can be attached to the opening provided by the removal of the screw (34) through which fleas can be drawn from outside the container (2), into the container (2) The screw (34) can be replaced after an appropriate number of fleas have been sucked into the container (2). Additional optional components suitable for the maintenance of fleas can be added to the container, such as animal hair. It is to be appreciated that other hematophagous arthropods can be loaded into containers of the present invention in similar manners.

In a preferred embodiment, a container of the present invention can be attached to an animal in the following manner. The animal is shaved where the container is to be placed in order to facilitate feeding by hematophagous arthropods retained in the container. A tubular bandage of the present invention is pulled onto a desired portion of the animal. One or more containers containing hematophagous arthropods is attached to the animal in a manner such that the confined hematophagous arthropods are able to feed undisturbed directly from the animal through the retaining means of the container. To do so, each container is placed between the tubular bandage and the skin of the animal such that the retaining means of each container is pressed against the skin of the animal. Each container is further secured to the animal by wrapping a wrapper, preferably self-adhesive, over the length of the tubular bandage in order to immobilize the container on the animal. The exchange means of the container usually adjoins the bandage, thereby enabling an exchange of gas, heat and humidity in and out of the container through the tubular bandage and wrapper.

In accordance with the present invention, a container can be attached to any site on an animal's body to which the container can be immobilized and where the container does not disturb the animal. Attachment sites on the lateral side of an animal are preferred. Attachment sites on the rib cage and/or the abdomen of an animal are more preferred. Preferably, from about 1 to about 4 containers are attached per animal, depending on the size of the animal and of the containers. More preferably about two containers are attached per animal.

In accordance with the present invention, containers are kept on an animal for a sufficient period of time to enable survival rates and fecundity levels to be determined for the hematophagous arthropods maintained in the container. While the time period can vary depending on the nature of use of the bioassay system, containers can be kept on animals for at least about 7 days and preferably for at least about 14 days. Containers can be kept for longer than 14 days. However, such periods may not be necessary because an effective agent should show results within 14 days. Most studies to, for example, evaluate flea biology or to test the efficacy of potential inhibitory agents preferably last about 7 to about 10 days. During such a time period, containers can be removed and reattached to the animals (i.e., the containers are reversibly detachable, and reversibly attachable) in order to obtain data about survival, fecundity, feeding and other parameters during the course of the study.

Survival rates, fecundity and other biological parameters of hematophagous arthropods maintained in a bioassay system of the present invention can be determined using techniques known to those skilled in the art. For example, the survival rate of hematophagous arthropods maintained over a defined period of time can be determined by assessing (e.g., counting) the number of hematophagous arthropods alive in the container after the appropriate period of time and comparing that number to the initial number of live hematophagous arthropods introduced into the container. As heretofore disclosed, fecundity can be measured by counting the number of eggs laid and relating that number to, for example, the number of eggs laid per number of female hematophagous arthropods in the container and/or to the average or maximum number of eggs laid per female per day. Hematophagous arthropods and/or eggs laid by such hematophagous arthropods can be counted daily or at any other suitable time interval.

The present invention can be used in a variety of applications whenever there is a need to evaluate hematophagous arthropod biological functions. Such applications include, but are not limited to, identifying agents that inhibit hematophagous arthropod infestation, testing an animal's resistance to hematophagous arthropod challenge, tracing the transmission of disease from hematophagous arthropod vector to host, evaluating different vector to host associations, and studying the effect of changing environmental conditions on the biological function of hematophagous arthropods. In a particularly preferred embodiment, bioassay systems of the present invention are used to study biological functions, such as those disclosed herein, of fleas.

In one embodiment, bioassay systems of the present invention can be used to study transmission of disease from hematophagous arthropod vector to host. As is true for a number of such vectors, fleas can be both primary and intermediate vectors for a variety of infectious agents which cause disease in animals, including humans. For example, fleas are known to carry *Rickettsia typhi* which causes endemic typhus in humans and *Yersinia pestis* which causes plague. Fleas also can act as intermediate hosts for cestodes and nematodes. Fleas can transmit infectious entities when they feed on a host, passing such entities from the gut of the flea into the bloodstream of the host. Bioassay systems of the present invention can be used to study the flea to host cycle in transmission of disease in the following manner. Fleas known to carry infectious entities are placed in a container which, in accordance with the present invention, is attached to a host known to be susceptible to the infectious entity. As used herein, a susceptible host refers to an animal that develops disease when infected by an infectious entity. For example, *Xenopsylla cheopis* fleas infected with *Yersinia pestis* (the bacterium that causes bubonic plague) can be added to a container which is then attached to a rat because rats develop disease when infected with *Y. pestis*. Factors affecting infection of the host can be studied and identified. Such factors can include the number of fleas required to cause disease and the amount of flea feeding time required to transmit the infectious entity.

In another embodiment, bioassay systems of the present invention can be used to study infection of hematophagous arthropods by hosts infected with a suitable infectious entity. For example, uninfected *Xenopsylla cheopis* fleas can be placed in a container which is then attached to a rat known to be infected with *Y. pestis*. Factors influencing acquisition of the infectious entity by the fleas can be determined, such as the amount of time the flea feeds until the flea acquires the infectious entity.

Bioassay systems of the present invention also can be used to identify vector-host pathogen associations such as those described above. For example, a pre-determined species of flea carrying a known infectious entity can be added to a series of containers and each container can be attached to a different type of animal. The degree of susceptibility of an animal to the infectious entity can be determined by, for example, the number of fleas and the minimum feeding time required for infection of the host. As such, containers can remain on the host animal for varying amounts of time until propagation of the infectious entity is detected in the host or disease symptoms develop.

A bioassay system can also be used to identify hematophagous arthropods thought to be carriers of infectious entities by adding suspect carriers to a container, attaching the container to a susceptible host, and inspecting the host for the presence of the infectious entity or for symptoms of the disease caused by the infectious entity.

The present invention includes a kit and a method to identify and/or measure the efficacy of agents that inhibit hematophagous arthropod infestation. The kit and method use bioassay systems of the present invention. Inhibitory agents can include any agent identified by the method of the present invention that is capable of protecting an animal from infestation by one or more species of hematophagous arthropods. As used herein, an inhibitory agent, or an agent capable of protecting an animal from hematophagous arthropod infestation, refers to an agent that is able to substantially prevent attack on a host and/or to reduce, or inhibit, the ability of one or more species of hematophagous arthropods to subsist on a host animal. Hematophagous arthropod infestation refers to attack of a host by that hematophagous arthropod resulting in colonization as well as subsistence of the hematophagous arthropod on a host animal over time which can lead to, for example, bites, allergy, and/or disease transmission. A putative inhibitory agent is an agent that is being tested to determine if it is capable of protecting an animal from hematophagous arthropod infestation. The ability of an agent to inhibit infestation (i.e., to protect an animal from infestation) can be measured by determining the effect of the agent on the biological functions of the hematophagous arthropods against which the agent is being developed, such as the ability of the agent to reduce fecundity, survival and feeding. In a preferred embodiment, inhibitory agents are lethal to the targeted hematophagous arthropods. Preferably, a kit and/or method of the present invention can be used to identify systemic agents.

In one embodiment, at least one container, or other holder, of the present invention having a pre-determined number of hematophagous arthropods is attached, in accordance with the present invention, to at least one animal that has been treated with (i.e., administered) a putative inhibitory agent. At least one container, or other holder, having a pre-determined number of hematophagous arthropods is also attached to at least one animal that has not been exposed to the putative inhibitory agent (i.e., an untreated animal). Preferably, treated and untreated animals share similar characteristics, such as being of similar breed, weight, size, health status and sex. It should be noted, however, that not animals participating in the study need to be in the study simultaneously; for example, it is possible to have obtained sufficient data on untreated animals so as not to require such a control in each study protocol.

Techniques to administer agents and to determine appropriate dosage, delivery and administration protocols are known to those skilled in the art. Retained hematophagous arthropods are permitted to feed from treated and untreated animals for a sufficient amount of time to determine the survival rate of the hematophagous arthropods (i.e., for an amount of time that allows distinctions in survival rates between hematophagous arthropods feeding from animals treated with known inhibitory agents, such as the anti-flea agent Proban® (cythioate), compared to hematophagous arthropods feeding from untreated animals).

The ability of the administered putative inhibitory agent to inhibit infestation by a hematophagous arthropod can be determined by comparing a biological function of such hematophagous arthropods retained in containers attached to treated animals with the function of such hematophagous arthropods retained in containers attached to untreated animals. For example, one can compare the survival rate of the hematophagous arthropods retained in containers attached to treated animals with the survival rate of the hematophagous arthropods retained in containers attached to untreated animals. Putative inhibitory agents that reduce the survival rate of the hematophagous arthropods by at least about 10 percent over a period of about 7 days after the containers are attached to the animals are considered inhibitory agents according to the present invention. Preferred inhibitory agents reduce the survival rate of the hematophagous arthropods by at least about 80 percent, and more preferably by about 100 percent, over about 7 days; and more preferred inhibitory agents reduce the survival rate of the hematophagous arthropods by at least about 80 percent and more preferably by about 100 percent over about 3 days. Particularly preferred inhibitory agents are those that reduce fleas survival by about 100 percent over about 7 days and more preferably over about 3 days.

The ability of a putative inhibitory compound to inhibit hematophagous arthropod infestation can also be determined by comparing the fecundity of such hematophagous arthropods retained in containers attached to treated animals with the fecundity of hematophagous arthropods retained in containers attached to untreated animals. Putative inhibitory agents that reduce the fecundity of hematophagous arthropods by at least about 15 percent are considered inhibitory agents according to the present invention. Preferred inhibitory agents reduce the fecundity of hematophagous arthropods, and particularly of fleas, by at least about 50 percent; more preferred inhibitory agents reduce the fecundity of hematophagous arthropods, and particularly of fleas, by at least about 80 percent; and even more preferred inhibitory agents reduce the fecundity of hematophagous arthropods, and particularly of fleas, by at least about 95 percent.

Another aspect of the present invention is a kit useful for the determining of an agent to inhibit infestation by a hematophagous arthropod. A kit comprises a bioassay system of the present invention. The bioassay system comprises at least one container, or other holder, of the present invention as heretofore described and a means for attaching the container to an animal as heretofore described. A kit of the present invention further comprises a means for determining the ability of a putative agent to inhibit hematophagous arthropod infestation. The ability of an agent to inhibit hematophagous arthropod infestation can be determined by counting the number of live and dead hematophagous arthropods retained in a container attached to an animal treated with a putative inhibitory agent to determine the survival rate. The survival rate of hematophagous arthropods feeding from animals treated with a putative inhibitory agent can be compared with the survival rate of hematophagous arthropods feeding from animals not treated with the agent. A lower survival rate is indicative of effective inhibitory activity by the putative agent. Preferred percent decreases in survival rate are heretofore disclosed. In another embodiment, fecundities can be measured and compared.

Assay kits and methods of the present invention can be used to determine the ability of a wide variety of agents to inhibit hematophagous arthropod infestation. Suitable agents to test include, but are not limited to, vaccines, drugs, hematophagous arthropod pathogens, systemic pesticides and hematophagous arthropod hormones. Preferred agents to test include vaccines and systemic pesticides.

As used herein, a vaccine refers to an agent that elicits an immune response against one or more particular antigens comprising the vaccine. Vaccines can be attenuated organisms, killed organisms, and/or suspensions of naturally-derived or recombinantly-derived subunits, such as proteins, carbohydrates, or other efficacious epitopes. A preferred vaccine of the present invention and method for making the same is described by Arfsten et al. in PCT International Publication No. WO 93/11790, published Jun. 24, 1993, which is incorporated herein in its entirety. As used herein, the term drug refers to any chemical compound that may be administered to an animal as an aid in preventing, treating or ameliorating infestation by a hematophagous arthropod. Drugs can be synthetic or natural compounds, and can include insecticides, such as Proban® and juvenile hormone analogues such as fenthion. As used herein, a hematophagous arthropod pathogen refers to any microorganism detrimental to a hematophagous arthropod.

The present invention also includes inhibitory agents capable of protecting an animal from hematophagous arthropod infestation, such inhibitory agents being identified by the kits and methods heretofore disclosed. Preferred inhibitory agents can protect any susceptible animal from infestation, such as, but not limited to, cats, dogs, humans, rabbits, sheep, cattle, swine, goats and opossums as well as other pets, economic food animals and animals that are hosts for hematophagous arthropods that infest pets and economic food animals. A particularly preferred inhibitory agent protects animals from infestation by a flea, such as by C. felis.

Another embodiment of the present invention is a method to test an animal's resistance to hematophagous arthropod challenge. Resistance can be genetic (i.e., natural resistance) or a vaccine-derived resistance. As used herein, hematophagous arthropod challenge refers to allowing one or more species of hematophagous arthropod to attempt to colonize and otherwise infest an animal host. An animal's resistance to such challenge can be tested by a method that includes (a) attaching a container of the present invention having a pre-determined number of hematophagous arthropods to an animal in such a manner that the confined hematophagous arthropods can feed directly from the animal through the container and that the container is immobilized to the animal (i.e., in accordance with the present invention) and (b) keeping the container attached on the animal for a sufficient amount of time to determine the survival rate of the confined hematophagous arthropods. Lower survival rates of the confined hematophagous arthropods, compared to survival rates on non-resistant animals, indicates higher resistance of the animal to hematophagous arthropod challenge.

The following experimental results are provided for purposes of illustration and are not intended to limit the scope of the invention.

EXAMPLES

Example 1

This example demonstrates that a bioassay system of the present invention supports significant fecundity levels and survival rates of fleas confined for at least about 7 days.

Two separate experiments (Study 1 and Study 2) were performed to test fecundity and survival rates of fleas confined in bioassay systems of the present invention for a defined period of time. Ten containers were prepared for each experiment. Containers were obtained from FleaData Inc. (Freeville, N.Y.) and the top portions of the containers were modified as follows. Referring to FIG. 2, the retaining means was removed from the smaller diameter part (20) of the first portion (8) of the purchased container. A new retaining means consisting of a nylon screen through which fleas could feed, but which retained fleas and flea eggs (e.g., screen having about 0.40 mm openings) was attached to the first top end (12) using Duco® glue. The bottom portion of the container was fitted with an exchange means consisting of a finer mesh nylon screen (e.g., screen having about 0.14 mm openings). The container had a height of about 2.0 mm and a diameter of about 6.5 mm. An average of about 50 *C. felis* fleas, of which an average of about 70 percent were females and about 30 percent were males, were inserted into each container. The top and bottom portions of the containers that were secured together after inserting fleas. Each container was attached to the shaved rib cage of a cat, using a tubular stretchable bandage and a wrapper as follows. Specifically, an about 8-inch long by about 2-inch diameter tubular surgical stockinette was pulled over the hind legs of the cat and placed over the shaved area. One of the flea-containing containers was then inserted between the stockinette against the skin of the cat such that the fleas were capable of feeding on the cat through the container (i.e., the retaining means of the container was in direct contact with the skin of the cat). Referring to FIG. 3, the container (42) was further secured by wrapping Vetrap® (44) about 6 times (using about ½ to ⅔ of a roll) over the stockinette in order to immobilize the container (42) on the cat. As such, the fleas confined in the container were able to feed undisturbed through the container directly from the cat.

The attached containers were kept on the cats for 3 days, at which time the containers were removed. The live and dead fleas in the container were counted and sexed; in addition, the number of eggs in the container were counted. The live fleas were subsequently re-inserted into a clean container, and the container attached to a different shaved site on the rib cage of the same animal. The attached containers were kept on the cats for an additional 4 days, at which time the containers were removed and the number and sex of the live and dead fleas was determined, as was the number of eggs laid.

Table 1 presents fecundity and survival results of fleas maintained in bioassay systems of the present invention during Study 1. Table 2 presents fecundity and survival results for Study 2. In summary, the average (or mean) number of eggs laid per female per day during the time period spanning days 1 through 3 was calculated to be 9.95 eggs/female/day for Study 1 and 11.37 eggs/female/day for Study 2. The average number of eggs laid per female per day during the time period spanning days 4 through 7 was calculated to be 22.08 eggs/female/day for Study 1 and 24.21 eggs/female/day for Study 2. In Study 1, an average of about 88.89% of the female fleas, and of about 97.48% of the male fleas, survived from the beginning of the study through day 3, whereas an average of about 88.60% of the female fleas, and of about 96.23% of the male fleas, survived from the beginning of the study through day 7. For Study 2, an average of about 95.56% of the female fleas, and of about 97.24% of the male fleas, survived from the beginning of the study through day 3, whereas an

TABLE 1

Flea Fecundity and Survival Results Study 1

| Samples | Fleas Put In Container at Start of Day 1 | | # Live Fleas at Day 3 | | # Eggs Laid (Day 1– Day 3) | # Live Fleas at Day 7 | | # Eggs Laid (Day 4– Day 7) |
|---|---|---|---|---|---|---|---|---|
| | ♂ | ♀ | ♂ | ♀ | | ♂ | ♀ | |
| 2941 | 15 | 37 | 15 | 34 | 1303 | 15 | 34 | 2982 |
| 2942 | 17 | 32 | 17 | 26 | 769 | 17 | 26 | 2008 |
| 2943 | 16 | 38 | 15 | 30 | 783 | 15 | 30 | 2745 |
| 2944 | 19 | 34 | 18 | 31 | 915 | 18 | 31 | 2927 |
| 2946 | 16 | 33 | 16 | 30 | 1085 | 16 | 30 | 2787 |
| 2947 | 17 | 35 | 17 | 35 | 1257 | 17 | 35 | 3102 |
| 2948 | 15 | 36 | 14 | 36 | 1418 | 14 | 35 | 3465 |
| 2956 | 16 | 37 | 16 | 30 | 960 | 15 | 30 | 2506 |
| 2458 | 13 | 36 | 12 | 31 | 997 | 12 | 31 | 2430 |
| 2961 | 15 | 33 | 15 | 29 | 994 | 14 | 29 | 2598 |

TABLE 2

Flea Fecundity and Survival Results Study 2

| Samples | Fleas Put In Container at Start of Day 1 | | # Live Fleas at Day 3 | | # Eggs Laid (Day 1– Day 3) | # Live Fleas at Day 7 | | # Eggs Laid (Day 4– Day 7) |
|---|---|---|---|---|---|---|---|---|
| | ♂ | ♀ | ♂ | ♀ | | ♂ | ♀ | |
| 2941 | 14 | 32 | 14 | 31 | 1293 | 14 | 31 | 3036 |
| 2942 | 14 | 37 | 13 | 35 | 1057 | 13 | 35 | 3282 |
| 2943 | 12 | 36 | 12 | 36 | 1070 | 12 | 36 | 3079 |
| 2944 | 12 | 35 | 12 | 33 | 1136 | 12 | 33 | 3182 |
| 2946 | 12 | 38 | 12 | 35 | 1192 | 11 | 34 | 3230 |
| 2947 | 27 | 38 | 26 | 34 | 1243 | 26 | 34 | 3878 |
| 2948 | 14 | 35 | 14 | 32 | 1159 | 14 | 32 | — |
| 2956 | 14 | 39 | 13 | 39 | 1431 | 12 | 39 | 3993 |
| 2458 | 12 | 37 | 12 | 37 | 1327 | 12 | 37 | 3374 |
| 2961 | 14 | 34 | 13 | 33 | 1067 | 13 | 33 | 3455 | average of about 95.29% of the female fleas, and of about 95.86% of the male fleas, survived from the beginning of the study through day 7. Note that essentially all fleas were accounted for (either as being dead or alive).

The results from Study 1 and Study 2 indicate that fleas confined in a bioassay system of the present invention laid an average of about 22 to about 24 eggs per female per day between days 4 and 7, which represents a fecundity significantly higher than that reported using other systems. In addition, the survival rates of fleas during the 7 day time period was, on average, greater than about 90%. The results indicate that bioassay systems of the present invention provide a permissive microenvironment that supports significant fecundity levels and survival rates of fleas confined in the system for at least about 7 days.

Example 2

This example demonstrates that a bioassay system of the present invention supports significant fecundity levels and survival rates of fleas confined for at least about 14 days.

Four containers were prepared as described in Example 1. An average of about 50 *C. felis* fleas, of which an average of about 70 percent were females and about 30 percent were males, were inserted into each container. Containers were attached to cats as described in Example 1. A pool of 10 cats was used to feed the fleas in the 4 containers for 14 consecutive days. Each day at approximately the same time, containers were removed from the cats; the number of live and dead fleas was determined as was the number of eggs laid. Live fleas were removed from the containers, placed in clean containers and attached to different cats within 90 minutes. In this manner, daily fecundities and survival rates were determined. On day 14, the containers were removed from the cats and the live fleas were collected, frozen, sexed and counted; the number of eggs laid was also determined.

Table 3 depicts the total number of fleas put into containers on day 1, the number of male and female fleas that survived each day, the total number of eggs laid each day and the average number of eggs laid per female each day.

TABLE 3

Flea Fecundity and Survival Results

| Day | # ♀♀ | # ♂♂ | # Eggs | Eggs/♀ |
|---|---|---|---|---|
| 1 | 137 | 59 | 0 | 0 |
| 2 | 135 | 57 | 1279 | 9.47 |
| 3 | 134 | 57 | 2701 | 20.16 |
| 4 | 127 | 56 | 2684 | 21.13 |
| 5 | 127 | 55 | 2729 | 21.49 |
| 6 | 127 | 55 | 2846 | 22.41 |
| 7 | 125 | 53 | 2957 | 23.66 |
| 8 | 125 | 51 | 2904 | 23.23 |
| 9 | 124 | 47 | 2556 | 20.61 |
| 10 | 120 | 45 | 2177 | 18.14 |
| 11 | 114 | 42 | 2300 | 20.18 |
| 12 | 111 | 42 | 2140 | 19.28 |
| 13 | 104 | 38 | 2632 | 25.31 |
| 14 | 102 | 38 | 2020 | 19.80 |

These results indicate that fleas maintained in bioassay systems of the present invention have essentially the same fecundity at day 14 as at day 3: The average number of eggs per female per day for all 4 containers during days 4 through 7 (i.e., 22.170±1.129 eggs/female/day) was very similar to the average number of eggs laid per female per day during days 4 through 14 (i.e., 21.280±2.045 eggs/female/day). These average fecundity values are also quite similar to those reported in Studies 1 and 2 of Example 1. As expected, the average number of eggs laid per female per day during the first three days (i.e., 9.877±10.090 eggs/female/day) was significantly lower than the average number of eggs laid per female per day after day 3. The high standard deviation value during the first three days is a result of fleas typically not laying a maximal number of eggs until about three days after beginning to feed. Approximately 89.83% of the female fleas and about 91.24% of the male fleas survived through day 7. About 64.41% of the female fleas and about 74.45% of the male fleas survived over the entire 14-day study.

These results indicate that the bioassay system of the present invention is capable of maintaining fleas for at least 14 days in an environment in which the average number of eggs laid per flea per day from day 4 through day 14 is substantially constant. Moreover, the average fecundity values obtained in this study (about 21 to 22 eggs per female per day) are significantly higher than those reported for other systems involving confined fleas. The ability to maintain fleas for a 14 day period is also significant in that 14 days should be a sufficiently long time to conduct efficacy trials of potential agents to inhibit flea infestation.

Example 3

The studies described in this Example illustrate the difficulty in devising a useful bioassay system for fleas, including the influence of container design and attachment means on the fecundity and survival rates of fleas maintained in such containers. These studies also demonstrate the importance of keeping flea containers immobilized on an animal.

A. Container designs

Several container designs were tested in this study. Container housings tested included small plastic weigh boats and plastic petri dishes of various sizes as well as plexiglass cylinders. Retaining and exchange means tested included Parafilm®, organdy cloth and several mesh sizes of plastic or nylon screens. The only container found to support fleas on a cat after attachment was a plexiglass-based container such as that described in Example 1.

In one set of experiments, three containers were prepared. The first container, into which 10 C. felis fleas were inserted, was a small plastic weigh boat (about 90 mm×90 mm×25 mm) having an organdy membrane to retain the fleas. The second container, into which about 50 C. felis fleas were inserted, was a medium-sized plastic petri dish (diameter of about 40 mm, height of about 12 mm) having a nylon membrane to retain the fleas. The third container, into which about 50 C. felis fleas were inserted, was a plexiglass container similar to that of Example 1 except that the retaining and exchange means comprised acrylic membranes. Each of these three containers was attached to the shaved abdomen of a cat (one container per cat) with Vetrap® (available from 3M Company Animal Care Products, St. Paul, Minn.). A fourth container, similar to the third container, was wrapped to a pole in the same room as the cats, as a control; the fourth container also had about 50 C. felis fleas.

Within two days, the small weigh boat container and the petri dish container fell off the cats and were destroyed. The plexiglass containers were removed from the cat and pole after 4 days. The number of live and dead fleas, number of eggs, and weight of eggs and feces contained in the containers were counted. The results are summarized in Table 4.

TABLE 4

Flea Fecundity in Plexiglass Container

| Cage | # Alive | # Dead | # Eggs | Wt. Egg + Feces | # Eggs/ ♀/Day |
|---|---|---|---|---|---|
| Plexiglass Container | 50 | 1 female | 1914 | 0.599 g | 9.57 |
| Control Container | 28 | 2 males 21 females | no eggs | no feces | |

In determining fecundity values (# Eggs/female/day) all female fleas (both alive and dead) are included. As such, the values are conservative representations of flea fecundity. The results indicate that the fleas retained in the plexiglass container attached to a cat were able to feed directly from the cat in such a manner that about 98% of the fleas survived after 4 days, the fleas produced feces, and the female fleas were able to produce eggs. In contrast, fleas retained in the plexiglass container attached to the pole demonstrated a 56% survival rate, and produced no detectable eggs or feces after 4 days. Thus, the plexiglass container and the method of attaching the container to an animal provides an environment in which fleas retained in the container demonstrate survival rates and fecundity levels significantly higher than the survival rates and fecundity levels of fleas not allowed to feed on an animal.

During the 4 days, however, it was found that the containers continually migrated towards the groin area of the cats and that the edges of the containers irritated the skin of the cats. In addition, the Vetrap® caused mild abrasions to the skin of the cats where the cats had been shaved and in the groin area. In addition, comparison of these results with those in which flea-containing containers are attached to cats as described in Example 1 and 2 indicates that Vetrap® alone is not as good an attachment means as that described in Examples 1 and 2. The lower fecundity levels seen in this experiment are likely to be due, at least in part, to the inability to keep the container immobilized.

B. Binding of container to abdomen by Vetrap®

Since the plexiglass container described in Example 3A produced the best results of the 3 containers tested in Example 3A, the ability of that plexiglass container (i.e., a plexiglass container with acrylic membranes) and the method of attaching the container to a cat in order to maintain fleas over a 7 day period was investigated.

Approximately 50 *C. felis* fleas were added to each of 5 plexiglass containers as described in Example 3A. Four containers were attached to 4 cats in the manner described in Example 3A. The fifth container was attached to a pole for control mortality assessment. The containers were removed from the cats and the pole after 3 days. In the case of the container on Cat #1, Cat #1 was a female cat in heat and continually rolled inside her cage. The rolling caused abrasions in her side resulting in the release of serum from her wounds. The serum seeped into the feeding membrane of the container and dried, greatly reducing the area available for the fleas to feed through. This cat was not used for the remainder of the experiment (described below). The number of live and dead fleas as well as of eggs contained in the containers were counted. The results are summarized in Table 5.

TABLE 5

Flea Survival and Fecundity in Plexiglass Containers

| Cat | # Alive Day 3 | # Dead Day 3 | % Survival Day 3 | # Eggs | # Eggs/ ♀ | Comments |
|---|---|---|---|---|---|---|
| 1 | 46 | 5 | 90 | 60 | 2.7 | Dry serum stuck to cage |
| 2 | 37 | 2 | 95 | 152 | 5.4 | |
| 3 | 51 | 0 | 100 | 309 | 15.5 | Looked good |
| 4 | 49 | 1 | 98 | 225 | 16.1 | Looked good |
| Control | 23 | 27 | 78 | | | |

In this portion of the study, the average survival rate of fleas maintained in containers attached to cats was about 96% for the 3 day study, as compared to 78% for fleas maintained in containers not attached to cats. The average fecundity value between containers was about 9 eggs/female/day; however, the fecundity values varied widely between containers. In the case of Cat #2, movement of the container on Cat #2 may be responsible for the variation in fecundity value. Frequently, the container attached to Cat #2 moved on the animal as the Vetrap® securing the container relaxed. Such movement of the container disrupted flea feeding.

In order to determine fecundity and survival rates for days 4 through 7, the live fleas obtained at day 3 were returned to clean containers and replaced on the original cats (i.e., Cats #2, 3 and 4). The containers, which were attached to the cats as described above, remained on the cats for an additional 4 days. During the 4 day period, each day, the container attached to Cat #2 continuously slid toward the groin area. As such, the container was moved forward and placed over the ribs which had been previously shaved. The movement of the container was minimal after it had been attached to the rib area. The containers were removed at the end of the 4-day period, and the live and dead fleas were sexed and counted, and the number of eggs was counted. The results are summarized in Table 6.

TABLE 6

Flea Survival and Fecundity in Plexiglass Containers

| | # Alive | | # Dead | | % | # | # Eggs/ Female |
|---|---|---|---|---|---|---|---|
| Cat # | Female | Male | Female | Male | Viability | Eggs | Day 4–7 |
| 2 | 0 | 4 | 23 | 10 | 10 | 276 | 12.0 |
| 3 | 39 | 10 | 2 | 0 | 96 | 263 | 6.4 |
| 4 | 39 | 7 | 3 | 0 | 92 | 519 | 12.4 |
| Control | 1 | 1 | 18 | 3 | 4 | | |

The survival rate for fleas retained in the container attached to Cat #2 was low compared with the survival rate of fleas retained in containers attached to Cat #3 and Cat #4. The reduction in survival rate of fleas retained in the container attached to Cat #2 suggests that movement of the container may have significantly affected the ability of the confined fleas to feed. Although the average fecundity across all containers was about 10 eggs per female per day, the variability again was quite high. Such variability in data, both in flea survival and flea fecundity, suggest the need for an improved method to attach flea containers to cats that permits the collection of data without such great variability.

C. Attachment of container to rib area

Since, in Example 3B, it appeared that the container on Cat #2 was more stable when attached to the rib area than to the abdomen, a study was conducted in which all containers were attached to the rib area of cats.

Specifically, about 50 *C. felis* fleas were inserted into each of five plexiglass containers prepared as described in Example 3A. A container was attached to the rib area of each of three cats by wrapping a length of Vetrap® around the chest to anchor the container forward on the chest, as shown in FIG. 3. Two containers were attached to the rib area of a fourth cat in a similar manner, one of which fell off after 24 hours.

The remaining containers were removed after 3 days. The feeding membrane of the container attached to Cat #1 was found to be clogged with serum-like substance exuded by the cat. Following removal of the containers, the live and dead fleas were sexed and counted, and the number of eggs were counted. The results are summarized in Table 7. The eggs isolated from all containers attached to cats were clumped together with the feces indicating high humidity in that container.

TABLE 7

Flea Survival and Fecundity in Plexiglass
Containers Fastened Over Rib Area

| Cat # | # Alive Female | # Alive Male | # Dead Female | # Dead Male | % Viability to Day 3 | # Eggs | # Eggs/Female/Day Day 1–3 |
|---|---|---|---|---|---|---|---|
| 1 | 29 | 7 | 17 | 0 | 68 | 641 | 4.6 |
| 2(Container 1) | 0 | 0 | 0 | 4 | 92 | 30 | |
| (Container 2) | 43 | 4 | 0 | 2 | 96 | 796 | 6.2 |
| 3 | 42 | 6 | 0 | 8 | 86 | 1176 | 9.3 |
| 4 | 48 | 3 | 1 | 4 | 91 | 1420 | 9.7 |

The live fleas collected on Day 3 were transferred to clean containers and placed back on rib cage of the original cats for an additional 4 days. To alleviate clumping of eggs, an 8" length of tubular surgical stockinette (2" diameter) was pulled over the ribs of each cat to help absorb excess humidity. Each container was placed beneath the stockinette such that the fleas could feed on the cat directly through the retaining means of the container. The Vetrap® was then wrapped over the stockinette and container to further secure the container. There were no clumped eggs present when the stockinette was used.

The containers were removed from the cats after 4 days. Following removal of the containers, the live and dead fleas were sexed and counted, and the number of eggs were counted. The results are summarized in Table 8.

TABLE 8

Flea Survival and Fecundity in Plexiglass Containers
Covered with Stockinette and Fastened to Rib Area

| Cat # | # Alive Female | # Alive Male | # Dead Female | # Dead Male | % Viability Days 4–7 | # Eggs | # Eggs/Female/Day Day 4–7 |
|---|---|---|---|---|---|---|---|
| 1 | 26 | 4 | 3 | 1 | 59 | 1176 | 11.3 |
| 2 | 43 | 4 | 0 | 0 | 85 | 2761 | 16.1 |
| 3 | 40 | 6 | 2 | 0 | 92 | 2683 | 16.8 |
| 4 | 43 | 3 | 5 | 0 | 81 | 2738 | 15.9 |

The results indicate that the egg production increased from day 4 to day 7 compared with the egg production from day 1 to day 3 while the average survival rate remained essentially constant.

Example 4

This Example demonstrates the usefulness of a bioassay system of the present invention to test the efficacy of a flea insecticide administered to cats.

An average of about 50 C. felis fleas were placed in each of 12 containers prepared as described in Example 1. Each container was attached to a cat as described in Example 1. The cats were divided into three groups each of which was administered the following with their food both on the day that the containers were attached to the cats and three days later (Day 3): (a) 4 cats received the flea insecticide cythioate (tradename Proban®, available from American Cyanamid, Wayne, N.J.) at a concentration of about 1.0 ml (milliliters) cythioate per 10 lb. (pounds) body weight of each cat; (b) 4 cats received about 0.1 ml cythioate per 10 lb. body weight of the cat; and (c) 4 cats received no insecticide. The "high dose" of cythioate (i.e., 1.0 ml per 10 lb. body weight) is the dose typically used to treat dogs infested with free-roaming fleas.

All contained fleas feeding from cats administered the high dose of cythioate were dead within 72 hours of the initial administration of the insecticide. Only about 21% of contained fleas feeding from cats administered the 10-fold lower dose were alive 7 days after the start of the experiment (Day 7). In comparison, about 88% of contained fleas feeding from cats not administered the insecticide were still alive at Day 7.

These results are at least equivalent to those obtained in studies using free-roaming fleas. As such, bioassay systems of the present invention have utility in studies to assess the efficacy of anti-flea agents. Furthermore, the bioassay systems permit the recovery of all fleas, thereby allowing for the generation of more reliable and statistically significant data using fewer animals.

Example 5

This Example demonstrates the usefulness of a bioassay system of the present invention to test the efficacy of an anti-flea vaccine.

A fed-flea midgut supernatant antigen preparation was prepared as described in PCT International Publication No. WO 93/11790, by Heath et al., published Jun. 24, 1993, which is incorporated herein by reference in its entirety. The preparation contained about 1,000 µg of protein per ml of phosphate buffer.

The efficacy of such an antigen preparation in protecting cats from flea infestation was tested in the following manner. Each of 10 cats (referred to herein as "vaccinated cats") was administered, by intramuscular injection, about 100 µg of the fed-flea midgut supernatant antigen preparation in phosphate buffer with RIBI adjuvant. An additional 10 cats (referred to herein as "control cats") were administered phosphate buffer with RIBI adjuvant. Two booster injections were given at about 21 day intervals. About 7 days after administration of the second boost of vaccine, or buffer and adjuvant alone, containers, prepared as described in Example 1 and each containing an average of about 35 female and 15 male fleas, were attached to both vaccinated and control cats as described in Example 1 such that each cat had one container. The numbers of live and dead male and female fleas as well as the number of eggs laid by the fleas was evaluated on days 3 and 7. Results of the study are depicted in Table 9.

TABLE 9

Survival and Fecundity Among Fleas on Vaccinated or Control Cats, Days 0–7

|  | # Alive* Day 3 | | # Dead Day 3 | | # Eggs | Eggs/Female/Day | # Alive Day 7 | | # Eggs | Egg/Female/Day | % Viability |
|---|---|---|---|---|---|---|---|---|---|---|---|
|  | Female | Male | Female | Male | Day 3 | Days 1–3 | Female | Male | Day 7 | Days 4–7 | Days 1–7 |
| Given Vaccine | 32.6 | 14.9 | 2.6 | 0.2 | 978 | 9.27 | 32.4 | 14.9 | 2332 | 17.9 | 94% |
| Control | 31.2 | 15.5 | 3.9 | 0.4 | 1048 | 9.97 | 31.1 | 15.3 | 2755 | 22.1 | 91% |

*All values represent means values from 10 cats

In summary, the vaccine did not appear to affect the survival of fleas, at least within the 7-day study period; i.e., about 94% of fleas confined on vaccinated cats were still alive, as compared to about 91% of fleas confined on control cats. However, the study did show a significant difference in the fecundity of fleas confined on vaccinated cats as compared to fleas confined on control cats: The number of eggs laid per female flea per day between days 4 and 7 was reduced by about 19% ($t=3.445$, $p<0.05$) for fleas confined on vaccinated cats compared to fleas confined on control cats. That is, the average fecundity of fleas confined on vaccinated cats was about 17.9 eggs per female per day compared to a fecundity of about 22.1 eggs per female per day for fleas confined on control cats. This result, in addition to suggesting potential utility of the vaccine, also indicates the advantage of bioassay systems of the present invention in that, by permitting the recovery of essentially all fleas and eggs, the systems allow identification of even small effects of a potential vaccine in early testing.

A repetition of this 7-day study yielded a statistically significant reduction of about 16.5% ($t=1.74$, $p<0.005$) in fecundity for fleas confined to vaccinated, as opposed to control, cats. A third study, which was conducted for 14 days, demonstrated an about 15.8% reduction in fecundity for fleas confined on vaccinated, as opposed to control, cats.

In summary, the results reported in this Example suggest that vaccination with a fed-flea midgut supernatant antigen vaccine results in a reduction in egg laying ability of fleas. Such vaccination apparently does not result in flea mortality, at least at the dose used in these studies. These studies also indicate that bioassay systems of the present invention maintain fleas in an environment that allows the fleas to feed as they would if they were free-roaming on an animal (i.e., the fecundity of confined fleas is at least substantially equivalent to the fecundity of free-roaming fleas). A benefit of bioassay systems of the present invention is that all eggs and fleas can be accounted for (e.g., flea eggs are retained in the container), thereby allowing investigators to discern small, but real, differences between, for example, the functional biology of fleas on vaccinated, compared to non-vaccinated, animals. In addition, it is much easier to count the fleas and eggs than it is to collect fleas that have been free-roaming on an animal or to collect the eggs of free-roaming fleas as the eggs fall off the animal into the cage.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed:

1. A bioassay system for hematophagous arthropods, comprising at least one container that retains hematophagous arthropods and a means for elastically immobilizing said container to an animal in such a manner that hematophagous arthropods retained in said container can feed undisturbed on said animal through said container, wherein the fecundity of said retained hematophagous arthropods is at least substantially equivalent to the fecundity of hematophagous arthropods feeding freely on an animal.

2. The bioassay system of claim 1, wherein said container also retains eggs laid by said hematophagous arthropods.

3. The bioassay system of claim 1, wherein the survival rate of hematophagous arthropods retained in said container is at least substantially equivalent to the survival rate of unconfined hematophagous arthropods.

4. The bioassay system of claim 3, wherein at least about 90 percent of hematophagous arthropods in said container survive at least about 7 days.

5. The bioassay system of claim 3, wherein at least about 70 percent of hematophagous arthropods in said container survive at least about 14 days.

6. The bioassay system of claim 1, wherein said retained hematophagous arthropods are maintained at a humidity and temperature such that the fecundity of said retained hematophagous arthropods is at least substantially equivalent to the fecundity of unconfined hematophagous arthropods.

7. The bioassay system of claim 6, wherein the humidity of said system ranges from about 60 percent relative humidity to about 95 percent relative humidity.

8. The bioassay system of claim 6, wherein the temperature of said system ranges from about 25° C. to about 30° C.

9. The bioassay system of claim 1, wherein said container comprises at least one material selected from the group consisting of metal, rubber, plastic, wood and glass materials.

10. The bioassay system of claim 1, wherein said container comprises a retaining means penetrable by hematophagous arthropod mouth parts, said retaining means being operatively connected to a means for exchanging gas, humidity and heat between the interior environment of said container and the exterior environment.

11. The bioassay system of claim 10, wherein said retaining means comprises at least one material selected from the group consisting of metallic mesh, nylon mesh, cloth and plastic materials.

12. The bioassay system of claim 10, wherein said retaining means comprises nylon mesh having from about 0.25 mm to about 0.50 mm openings.

13. The bioassay system of claim 10, wherein said retaining means comprises nylon mesh having openings in the range of about 1 mm.

14. The bioassay system of claim 10, wherein said exchange means comprises at least one material selected from the group consisting of metallic mesh, nylon mesh, cloth and plastic materials.

15. The bioassay system of claim 10, wherein said exchange means comprises nylon mesh having from about 0.10 mm to about 0.45 mm openings.

16. The bioassay system of claim 1, wherein said immobilizing means allows the exchange of gas, heat and humidity such that the fecundity of hematophagous arthropods confined within said container is at least substantially equivalent to the fecundity of unconfined hematophagous arthropods.

17. The bioassay system of claim 1, wherein said immobilizing means comprises:
  (a) a bandage having sufficient size to wrap around the torso of an animal having an outer skin, said container being placed between said bandage and said outer skin of the animal; and
  (b) a wrapper operatively connected to said bandage in order to immobilize said container on said animal.

18. The bioassay system of claim 17, wherein said bandage comprises at least one material selected from the group consisting of cloth, plastic and tape.

19. The bioassay system of claim 17, wherein said bandage comprises at least one material selected from the group consisting of surgical stockinettes and cloth tape materials.

20. The bioassay system of claim 17, wherein said wrapper comprises a self-adhesive material.

21. The bioassay system of claim 1, wherein said animal is a vertebrate.

22. The bioassay system of claim 1, wherein said animal is a mammal.

23. The bioassay system of claim 1, wherein said animal is selected from the group consisting of cats, dogs, rabbits, humans, sheep, cattle, goats, swine, rats, raccoons, and opossums.

24. The bioassay system of claim 1, wherein said animal is a cat or a dog.

25. The bioassay system of claim 1, wherein said container is immobilized at a site on the animal such that said animal is not disturbed by said container.

26. The bioassay system of claim 1, wherein said container is immobilized to the lateral side of an animal.

27. The bioassay system of claim 1, wherein said container is immobilized to the rib cage of an animal.

28. The bioassay system of claim 1, wherein said container is immobilized to the abdomen of an animal.

29. The bioassay system of claim 1, wherein said hematophagous arthropods are selected from the group consisting of insects and arachnids.

30. The bioassay system of claim 1, wherein said hematophagous arthropods are selected from the group consisting of fleas, ticks, flies, lice and true bugs.

31. The bioassay system of claim 1, wherein said hematophagous arthropods are selected from the group consisting of fleas, ticks and flies.

32. The bioassay system of claim 1, wherein said hematophagous arthropods comprises fleas selected from the group consisting of *Ctenocephalides felis, Ctenocephalides canis, Echidnophaga gallinacea, Pulex irritans, Pulex simulans, Xenopsylla cheopis* and *Oropsylla* (*Diamanus*) *montana*.

33. The bioassay system of claim 1, wherein said container can maintain at least about 100 fleas per container.

34. The bioassay system of claim 1, wherein the number of eggs produced per female hematophagous arthropod on about the fourth day of retention in said container is about equivalent to the number of eggs produced per female on about the fourteenth day of retention in said container.

35. The bioassay system of claim 1, wherein fleas retained in said container produce an average of at least about 18 eggs per female flea per day from about the fourth day of retention through about the seventh day of retention.

36. The bioassay system of claim 1, wherein fleas retained in said container produce an average of at least about 18 eggs per female flea per day from about the fourth day of retention through about the fourteenth day of retention.

37. A bioassay system for hematophagous arthropods, comprising:
  (a) at least one container that retains hematophagous arthropods, said container being penetrable by the mouth parts of said hematophagous arthropods; and
  (b) a means for elastically immobilizing said container to an animal, wherein said immobilizing means allows hematophagous arthropods to feed undisturbed on said animal through said container and wherein the fecundity of hematophagous arthropods confined in said container is at least substantially equivalent to the fecundity of unconfined hematophagous arthropods feeding on an animal.

38. The bioassay system of claim 37, wherein said container retains eggs laid by said hematophagous arthropods.

39. The bioassay system of claim 37, wherein said container comprises a retaining means penetrable by said mouth parts operatively connected to a means for exchanging gas, humidity and heat between the interior environment of said container and the exterior environment.

40. The bioassay system of claim 37, wherein hematophagous arthropods confined in said container have a survival rate that is at least substantially equivalent to the survival rate of unconfined hematophagous arthropods.

41. A method for mimicking the natural conditions of hematophagous arthropods roaming free on an animal, comprising:
  (a) immobilizing to an animal at least one container that retains hematophagous arthropods by a means for elastically immobilizing said container to an animal such that hematophagous arthropods can feed undisturbed on said animal through said container; and
  (b) keeping said container immobilized on said animal for a defined period of time.

42. A bioassay system for fleas, comprising at least one container that retains fleas and flea eggs, and a means for elastically immobilizing said container to an animal in such a manner that fleas retained in said container can feed undisturbed on said animal through said container, wherein the fecundity of said retained fleas is at least substantially equivalent to the fecundity of fleas free-roaming on an animal.

43. The bioassay system of claim 42, wherein the survival rate of fleas retained in said container is at least substantially equivalent to the survival rate of unconfined fleas.

44. The bioassay system of claim 42, wherein said container comprises a retaining means penetrable by flea mouth parts operatively connected to a means for exchanging gas, humidity and heat between the interior environment of said container and the exterior environment.

45. The bioassay system of claim 42, wherein said immobilizing means comprises:
(a) a bandage having sufficient size to wrap around the torso of an animal having an outer skin, said container being placed between said bandage and said outer skin of the animal; and
(b) a wrapper operatively connected to said bandage in order to immobilize said container on said animal.

46. The bioassay system of claim 42, wherein the number of eggs produced per female flea on about the fourth day of retention in said container is about equivalent to the number of eggs produced per female on about the fourteenth day of retention in said container.

47. A flea bioassay system comprising at least one container that retains flea and flea eggs, and a means for elastically immobilizing said container to an animal, wherein the fecundity of fleas retained in said container is at least about equivalent to the fecundity of free-roaming fleas for at least 14 days.

48. The flea bioassay system of claim 47, wherein said system is of a humidity and temperature such that the fecundity of fleas confined within said container is at least substantially equivalent to the fecundity of fleas free-roaming on an animal.

49. The flea bioassay system of claim 47, wherein said container comprises a retaining means penetrable by the flea mouth parts operatively connected to a means for exchanging gas, humidity and heat between the interior environment of said container and the exterior environment.

50. The flea bioassay system of claim 47, wherein said immobilizing means secures said container to an animal in such a manner that said container remains immobile while attached to said animal.

* * * * *